(12) United States Patent
Linder et al.

(10) Patent No.: US 9,585,644 B2
(45) Date of Patent: *Mar. 7, 2017

(54) DEVICES FOR REDUCING THE SIZE OF AN INTERNAL TISSUE OPENING

(71) Applicant: Coherex Medical, Inc., Salt Lake City, UT (US)

(72) Inventors: Richard J. Linder, Sandy, UT (US); Clark C. Davis, Holladay, UT (US); Scott D. Miles, Sandy, UT (US); DeWayne C. Fox, South Jordan, UT (US); Daryl R. Edmiston, Draper, UT (US); David A. Ewell, West Jordan, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 328 days.

This patent is subject to a terminal disclaimer.

(21) Appl. No.: 14/023,462

(22) Filed: Sep. 10, 2013

(65) Prior Publication Data
US 2014/0172011 A1 Jun. 19, 2014

Related U.S. Application Data

(63) Continuation of application No. 12/783,498, filed on May 19, 2010, now Pat. No. 8,529,597, which is a (Continued)

(51) Int. Cl.
*A61B 17/00* (2006.01)
*A61B 17/12* (2006.01)

(52) U.S. Cl.
CPC .... *A61B 17/0057* (2013.01); *A61B 17/12122* (2013.01); *A61B 17/12172* (2013.01);
(Continued)

(58) Field of Classification Search
CPC ...... A61B 17/0057; A61B 2017/00575; A61B 2017/00606; A61B 2017/00597;
(Continued)

(56) References Cited

U.S. PATENT DOCUMENTS 2,755,060 A 7/1956 Twyman
3,874,388 A 4/1975 King et al.
(Continued)

FOREIGN PATENT DOCUMENTS

EP 0539125 4/1993
EP 0536610 9/1997
(Continued)

OTHER PUBLICATIONS

Intravascular Occluding Device ing a Modified Gianturco Stent as a Coil Cage. Wilson Gordon LaBerge Saavedra and Kerlan. JVIR. 2000.
(Continued)

Primary Examiner — Christopher L Templeton
(74) Attorney, Agent, or Firm — David L. Scott

(57) ABSTRACT

A medical system for treating an internal tissue opening can include a closure device and associated delivery device. The closure device can include a body portion operatively associated with a first anchor and a second anchor. The body portion can include a plurality of segments defining a multi-cellular structure. The closure device can be configured to apply lateral force to tissue of the internal tissue opening to bring tissue together. The closure device can have a substantially flat aspect, and have a depth thickness that is substantially greater than the thickness or width of a majority of the members forming the closure device to reduce out of plane bending. The closure device can also include a member adapted to induce tissue growth.

19 Claims, 21 Drawing Sheets

Related U.S. Application Data continuation-in-part of application No. 11/836,000, filed on Aug. 8, 2007, now Pat. No. 9,138,208, and a continuation-in-part of application No. 11/836,016, filed on Aug. 8, 2007, and a continuation-in-part of application No. 11/836,123, filed on Aug. 8, 2007, now Pat. No. 8,167,894.

(60) Provisional application No. 61/179,640, filed on May 19, 2009, provisional application No. 61/260,334, filed on Nov. 11, 2009, provisional application No. 60/821,947, filed on Aug. 9, 6, provisional application No. 60/829,507, filed on Oct. 13, 2006, provisional application No. 60/866,047, filed on Nov. 15, 2006, provisional application No. 60/942,625, filed on Jun. 7, 2007, provisional application No. 60/821,949, filed on Aug. 9, 2006.

(52) U.S. Cl.
CPC ............... *A61B 2017/0061* (2013.01); *A61B 2017/00084* (2013.01); *A61B 2017/00407* (2013.01); *A61B 2017/00575* (2013.01); *A61B 2017/00579* (2013.01); *A61B 2017/00592* (2013.01); *A61B 2017/00597* (2013.01); *A61B 2017/00606* (2013.01); *A61B 2017/00619* (2013.01); *A61B 2017/00623* (2013.01); *A61B 2017/00858* (2013.01); *A61B 2017/00862* (2013.01); *A61B 2017/00867* (2013.01)

(58) Field of Classification Search
CPC ....... A61B 2017/081; A61B 2017/0061; A61F 2/01; A61F 2/82; A61F 2/90; A61F 2/915; A61F 2/86; A61F 2/91; A61F 2002/9155; A61F 2002/075; A61F 2002/91533
See application file for complete search history.

(56) References Cited

U.S. PATENT DOCUMENTS

| | | |
|---|---|---|
| 4,007,743 A | 2/1977 | Blake |
| 4,708,140 A | 11/1987 | Baron |
| 4,762,129 A | 8/1988 | Bonzel |
| 4,840,185 A | 6/1989 | Hernandez |
| 4,917,089 A | 4/1990 | Sideris |
| 4,957,501 A | 9/1990 | Lahille et al. |
| 4,988,356 A | 1/1991 | Crittenden et al. |
| 5,002,531 A | 3/1991 | Bonzel |
| 5,040,548 A | 8/1991 | Yock |
| 5,041,093 A | 8/1991 | Chu |
| 5,108,420 A | 4/1992 | Marks |
| 5,171,259 A | 12/1992 | Inoue |
| 5,192,301 A | 3/1993 | Kamiya et al. |
| 5,217,450 A | 6/1993 | Prior et al. |
| 5,232,445 A | 8/1993 | Bonzel |
| 5,234,458 A | 8/1993 | Metais |
| 5,300,085 A | 4/1994 | Yock |
| 5,334,217 A | 8/1994 | Das |
| 5,339,803 A | 8/1994 | Mayzels et al. |
| 5,425,744 A | 6/1995 | Fagan et al. |
| 5,433,723 A | 7/1995 | Lindenberg et al. |
| 5,451,235 A | 9/1995 | Lock et al. |
| 5,484,449 A | 1/1996 | Amundson et al. |
| 5,496,277 A | 3/1996 | Termin et al. |
| 5,501,227 A | 3/1996 | Yock |
| 5,578,045 A | 11/1996 | Das |
| 5,634,931 A | 6/1997 | Kugel |
| 5,643,317 A | 7/1997 | Pavcnik et al. |
| 5,683,411 A | 11/1997 | Kavteladze et al. |
| 5,702,421 A | 12/1997 | Schneidt |
| 5,709,224 A | 1/1998 | Behl et al. |
| 5,725,552 A | 3/1998 | Kotula et al. |
| 5,741,297 A | 4/1998 | Simon |
| 5,766,184 A | 6/1998 | Matsuno et al. |
| 5,792,179 A | 8/1998 | Sideris |
| 5,846,261 A | 12/1998 | Kotula et al. |
| 5,853,422 A | 12/1998 | Huebsch et al. |
| 5,861,003 A | 1/1999 | Latson et al. |
| 5,879,366 A | 3/1999 | Shaw et al. |
| 5,887,594 A | 3/1999 | LoCicero |
| 5,904,703 A | 5/1999 | Gilson |
| 5,916,145 A | 6/1999 | Chu et al. |
| 5,944,738 A | 8/1999 | Amplatz et al. |
| 5,947,997 A | 9/1999 | Pavcnik et al. |
| 5,993,482 A | 11/1999 | Chuter |
| 5,993,484 A | 11/1999 | Shmulewitz |
| 6,004,328 A | 12/1999 | Solar |
| 6,007,563 A | 12/1999 | Nash et al. |
| 6,031,148 A | 2/2000 | Hayes et al. |
| 6,077,281 A | 6/2000 | Das |
| 6,077,291 A | 6/2000 | Das |
| 6,080,182 A | 6/2000 | Shaw et al. |
| 6,165,167 A | 12/2000 | Delaloye |
| 6,168,616 B1 | 1/2001 | Brown, III |
| 6,171,329 B1 | 1/2001 | Shaw et al. |
| 6,174,322 B1 | 1/2001 | Schneidt |
| 6,196,995 B1 | 3/2001 | Fagan |
| 6,200,336 B1 | 3/2001 | Pavcnik et al. |
| 6,206,907 B1 | 3/2001 | Marino et al. |
| 6,210,338 B1 | 4/2001 | Afremov et al. |
| 6,214,029 B1 | 4/2001 | Thill et al. |
| 6,241,678 B1 | 6/2001 | Afremov et al. |
| 6,267,777 B1 | 7/2001 | Bosma et al. |
| 6,273,901 B1 | 8/2001 | Whitcher et al. |
| 6,327,772 B1 | 12/2001 | Zadno-Azizi |
| 6,342,064 B1 | 1/2002 | Koike et al. |
| 6,355,052 B1 | 3/2002 | Neuss et al. |
| 6,368,339 B1 | 4/2002 | Amplatz |
| 6,375,671 B1 | 4/2002 | Kobayashi et al. |
| 6,379,368 B1 | 4/2002 | Corcoran et al. |
| 6,436,068 B1 | 8/2002 | Bardy |
| 6,440,152 B1 | 8/2002 | Gainor et al. |
| 6,482,221 B1 | 11/2002 | Hebert et al. |
| 6,506,190 B1 | 1/2003 | Walshe |
| 6,551,344 B2 | 4/2003 | Thill |
| 6,589,207 B1 | 7/2003 | El-Nounou |
| 6,592,549 B2 | 7/2003 | Gerdts et al. |
| 6,596,013 B2 | 7/2003 | Yang et al. |
| 6,605,062 B1 | 8/2003 | Hurley et al. |
| 6,605,109 B2 | 8/2003 | Fiedler |
| 6,613,075 B1 | 9/2003 | Healy et al. |
| 6,645,225 B1 | 11/2003 | Atkinson |
| 6,645,239 B1 | 11/2003 | Park et al. |
| 6,656,206 B2 | 12/2003 | Corcoran et al. |
| 6,679,909 B2 | 1/2004 | McIntosh et al. |
| 6,689,144 B2 | 2/2004 | Gerberding |
| 6,709,667 B1 | 3/2004 | Lowe et al. |
| 6,712,836 B1 | 3/2004 | Berg et al. |
| 6,723,071 B2 | 4/2004 | Gerdts et al. |
| 6,736,823 B2 | 5/2004 | Darois et al. |
| 6,743,210 B2 | 6/2004 | Hart et al. |
| 6,793,667 B2 | 9/2004 | Hebert et al. |
| 6,800,065 B2 | 10/2004 | Duane et al. |
| 6,837,894 B2 | 1/2005 | Pugsley et al. |
| 6,893,417 B2 | 5/2005 | Gribbons et al. |
| 6,932,832 B2 | 8/2005 | Patel et al. |
| 6,979,311 B2 | 12/2005 | Miles et al. |
| 6,979,991 B2 | 12/2005 | Burns et al. |
| 6,994,689 B1 | 2/2006 | Zadno-Azizi et al. |
| 7,011,645 B2 | 3/2006 | McGuckin et al. |
| 7,011,671 B2 | 3/2006 | Welch |
| 7,037,293 B2 | 5/2006 | Carrillo et al. |
| 7,087,088 B2 | 8/2006 | Berg et al. |
| 7,122,043 B2 | 10/2006 | Greenhalgh et al. |
| 7,137,990 B2 | 11/2006 | Hebert et al. |
| 7,144,410 B2 | 12/2006 | Marino et al. |
| 7,169,165 B2 | 1/2007 | Belef et al. |
| 7,179,252 B2 | 2/2007 | Agro et al. |

(56) References Cited

U.S. PATENT DOCUMENTS

| | | |
|---|---|---|
| 7,220,265 B2 | 5/2007 | Chanduszko et al. |
| 7,267,679 B2 | 9/2007 | McGuckin et al. |
| 7,288,105 B2 | 10/2007 | Oman et al. |
| 7,318,833 B2 | 1/2008 | Chanduszko |
| 7,323,006 B2 | 1/2008 | Andreas et al. |
| 7,377,936 B2 | 5/2008 | Gainor et al. |
| 7,708,755 B2 | 5/2010 | Davis, III et al. |
| 7,879,090 B2 | 2/2011 | Pynson |
| 8,062,325 B2 | 11/2011 | Mitelberg et al. |
| 2001/0007939 A1 | 7/2001 | Fleischman |
| 2001/0037129 A1 | 11/2001 | Thill |
| 2001/0037141 A1 | 11/2001 | Yee et al. |
| 2001/0039434 A1 | 11/2001 | Frazier et al. |
| 2002/0095141 A1 | 7/2002 | Belef et al. |
| 2002/0100485 A1 | 8/2002 | Stevens et al. |
| 2002/0111647 A1 | 8/2002 | Khairkhahan et al. |
| 2002/0169475 A1 | 11/2002 | Gainor et al. |
| 2003/0028213 A1 | 2/2003 | Thill et al. |
| 2003/0028235 A1 | 2/2003 | McIntosh et al. |
| 2003/0109886 A1 | 6/2003 | Keegan et al. |
| 2003/0139819 A1 | 7/2003 | Beer et al. |
| 2003/0167060 A1 | 9/2003 | Buzzard et al. |
| 2003/0171774 A1 | 9/2003 | Freudenthal et al. |
| 2003/0181942 A1 | 9/2003 | Sutton et al. |
| 2003/0191479 A1 | 10/2003 | Thornton et al. |
| 2003/0191495 A1 | 10/2003 | Ryan et al. |
| 2003/0195561 A1 | 10/2003 | Carley et al. |
| 2003/0199987 A1 | 10/2003 | Berg et al. |
| 2003/0208232 A1 | 11/2003 | Blaeser et al. |
| 2003/0220667 A1 | 11/2003 | van der Burg et al. |
| 2003/0225421 A1 | 12/2003 | Peavey et al. |
| 2004/0010285 A1 | 1/2004 | Carley et al. |
| 2004/0044361 A1 | 3/2004 | Frazier et al. |
| 2004/0073242 A1 | 4/2004 | Chanduszko |
| 2004/0073252 A1 | 4/2004 | Goldberg et al. |
| 2004/0098042 A1 | 5/2004 | Devellian et al. |
| 2004/0098094 A1* | 5/2004 | Boyle ............. A61F 2/07 623/1.13 |
| 2004/0111095 A1 | 6/2004 | Gordon et al. |
| 2004/0133236 A1 | 7/2004 | Chanduszko |
| 2004/0143294 A1 | 7/2004 | Corcoran et al. |
| 2004/0176799 A1 | 9/2004 | Chanduszko et al. |
| 2004/0220596 A1 | 11/2004 | Frazier et al. |
| 2004/0220610 A1 | 11/2004 | Kreidler et al. |
| 2004/0220612 A1 | 11/2004 | Swainston et al. |
| 2004/0225324 A1 | 11/2004 | Marino et al. |
| 2004/0254594 A1 | 12/2004 | Alfaro |
| 2004/0267191 A1 | 12/2004 | Gifford, III et al. |
| 2004/0267306 A1 | 12/2004 | Blaeser et al. |
| 2005/0027305 A1 | 2/2005 | Shiu et al. |
| 2005/0033327 A1 | 2/2005 | Gainor et al. |
| 2005/0034735 A1 | 2/2005 | Deem et al. |
| 2005/0049681 A1 | 3/2005 | Greenhalgh et al. |
| 2005/0055050 A1 | 3/2005 | Alfaro |
| 2005/0065547 A1 | 3/2005 | Marino et al. |
| 2005/0113902 A1 | 5/2005 | Geiser et al. |
| 2005/0119675 A1 | 6/2005 | Adams et al. |
| 2005/0125032 A1 | 6/2005 | Whisenant et al. |
| 2005/0192627 A1 | 9/2005 | Whisenant et al. |
| 2005/0222603 A1 | 10/2005 | Andreas et al. |
| 2005/0228434 A1 | 10/2005 | Amplatz et al. |
| 2005/0228475 A1 | 10/2005 | Keeble et al. |
| 2005/0234509 A1 | 10/2005 | Widomski et al. |
| 2005/0251154 A1 | 11/2005 | Chanduszko et al. |
| 2005/0251201 A1 | 11/2005 | Roue et al. |
| 2005/0256532 A1 | 11/2005 | Nayak et al. |
| 2005/0267524 A1 | 12/2005 | Chanduszko |
| 2005/0267525 A1 | 12/2005 | Chanduszko |
| 2005/0273119 A1 | 12/2005 | Widomski et al. |
| 2005/0288706 A1 | 12/2005 | Widomski et al. |
| 2005/0288786 A1 | 12/2005 | Chanduszko |
| 2006/0009799 A1 | 1/2006 | Kleshinski et al. |
| 2006/0106418 A1 | 5/2006 | Seibold et al. |
| 2006/0106420 A1 | 5/2006 | Dolan et al. |
| 2006/0116710 A1 | 6/2006 | Corcoran et al. |
| 2006/0122647 A1 | 6/2006 | Callaghan et al. |
| 2006/0178694 A1 | 8/2006 | Greenhalgh et al. |
| 2006/0200234 A1* | 9/2006 | Hines ............. A61B 17/12022 623/1.49 |
| 2006/0241675 A1* | 10/2006 | Johnson ............. A61F 2/01 606/200 |
| 2006/0271089 A1 | 11/2006 | Alejandro et al. |
| 2007/0073389 A1 | 3/2007 | Bolduc et al. |
| 2007/0100356 A1 | 5/2007 | Lucatero et al. |
| 2007/0106327 A1 | 5/2007 | Thill |
| 2007/0112382 A1 | 5/2007 | Thill |
| 2007/0123934 A1 | 5/2007 | Whisenant et al. |
| 2007/0129756 A1 | 6/2007 | Abbott et al. |
| 2007/0270905 A1 | 11/2007 | Osborne |
| 2008/0002927 A1 | 1/2008 | Furnish |
| 2008/0015636 A1 | 1/2008 | Olsen et al. |
| 2008/0039743 A1 | 2/2008 | Fox et al. |
| 2008/0039804 A1 | 2/2008 | Edmiston et al. |
| 2008/0039922 A1 | 2/2008 | Miles et al. |
| 2008/0039929 A1 | 2/2008 | Davis et al. |
| 2008/0039952 A1 | 2/2008 | Linder et al. |
| 2008/0039953 A1 | 2/2008 | Davis et al. |
| 2008/0058866 A1 | 3/2008 | Young et al. |
| 2008/0119891 A1 | 5/2008 | Miles et al. |
| 2008/0221668 A1 | 9/2008 | Pinchuk et al. |
| 2009/0270840 A1 | 10/2009 | Miles et al. |

FOREIGN PATENT DOCUMENTS

| | | |
|---|---|---|
| EP | 0541063 | 9/1998 |
| EP | 0545091 | 7/1999 |
| EP | 0614342 | 7/1999 |
| EP | 1013227 | 6/2000 |
| EP | 1046375 | 10/2000 |
| EP | 0474752 | 12/2000 |
| EP | 0861049 | 4/2001 |
| EP | 1175867 | 1/2002 |
| EP | 0698373 | 11/2003 |
| EP | 1595504 | 11/2005 |
| EP | 1179999 | 1/2006 |
| EP | 1211983 | 3/2007 |
| EP | 1864613 | 12/2007 |
| EP | 1222897 | 3/2008 |
| EP | 1923005 | 5/2008 |
| EP | 1923019 | 5/2008 |
| WO | 9808462 | 3/1998 |
| WO | 0149185 | 7/2001 |
| WO | 0245593 | 6/2002 |
| WO | 03068302 | 8/2003 |
| WO | 03082076 | 10/2003 |
| WO | 03103476 | 12/2003 |
| WO | 2004052213 | 6/2004 |
| WO | 2004091411 | 10/2004 |
| WO | 2004103162 | 12/2004 |
| WO | 2004103209 | 12/2004 |
| WO | 2005034738 | 4/2005 |
| WO | 2006036837 | 4/2006 |
| WO | 2006062711 | 6/2006 |
| WO | 2006093968 | 9/2006 |
| WO | 2006110147 | 10/2006 |
| WO | 2006130836 | 12/2006 |
| WO | 2007021647 | 2/2007 |
| WO | 2007028092 | 3/2007 |
| WO | 2007038608 | 4/2007 |
| WO | 2007038609 | 4/2007 |
| WO | 2007083288 | 7/2007 |
| WO | 2007092860 | 8/2007 |
| WO | 2007120186 | 10/2007 |
| WO | 2007136660 | 11/2007 |
| WO | 2007140419 | 12/2007 |
| WO | 2007140420 | 12/2007 |
| WO | 2008021969 | 2/2008 |
| WO | 2006028813 | 3/2008 |
| WO | 2008033309 | 3/2008 |
| WO | 2008040555 | 4/2008 |
| WO | 2008025405 | 6/2008 |

(56) References Cited

FOREIGN PATENT DOCUMENTS

WO  2008124603  10/2008
WO  2008125689  10/2008

OTHER PUBLICATIONS

Construction of Hydraulic Cuff Occluders for Blood Vessels. Shoukas Arin A. Department of Biomedical Engineering. Johns Hopkins University. 1976.
International Search Report dated Sep. 26, 2008 for International Application No. PCT/07/75611 (2 pages).
International Search Report dated Sep. 9, 2008 for International Application No. PCT/07/75608 (2 pages).
Supplementary European Search Report for European Application No. EP 07840828.3, mailed Apr. 15, 2013.
Extended European Search Report for European Application No. EP07840825, mailed Mar. 8, 2013.

\* cited by examiner

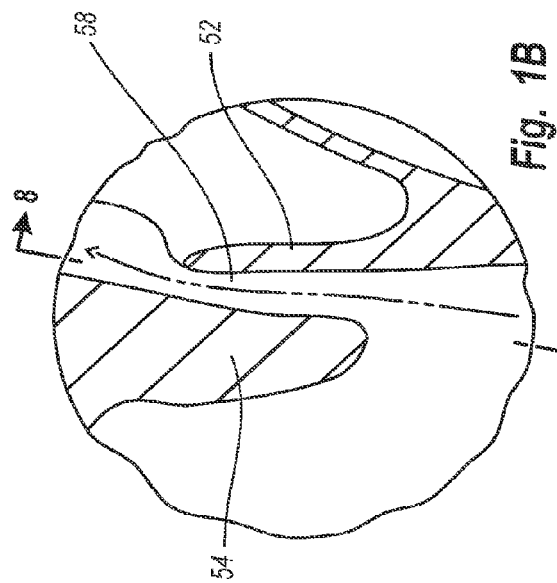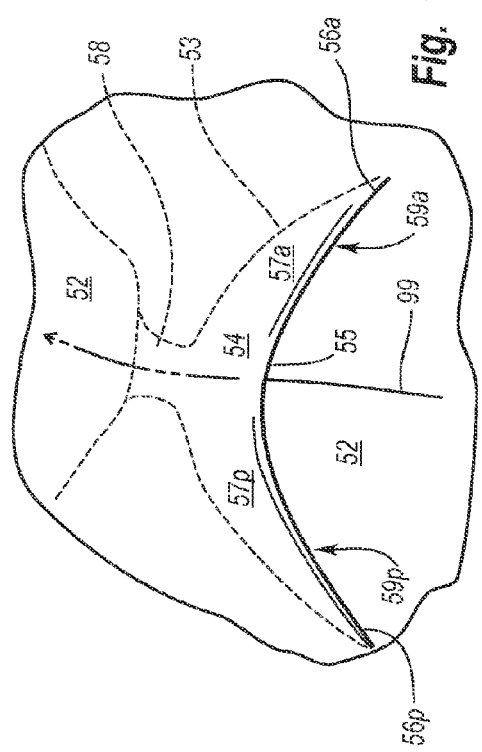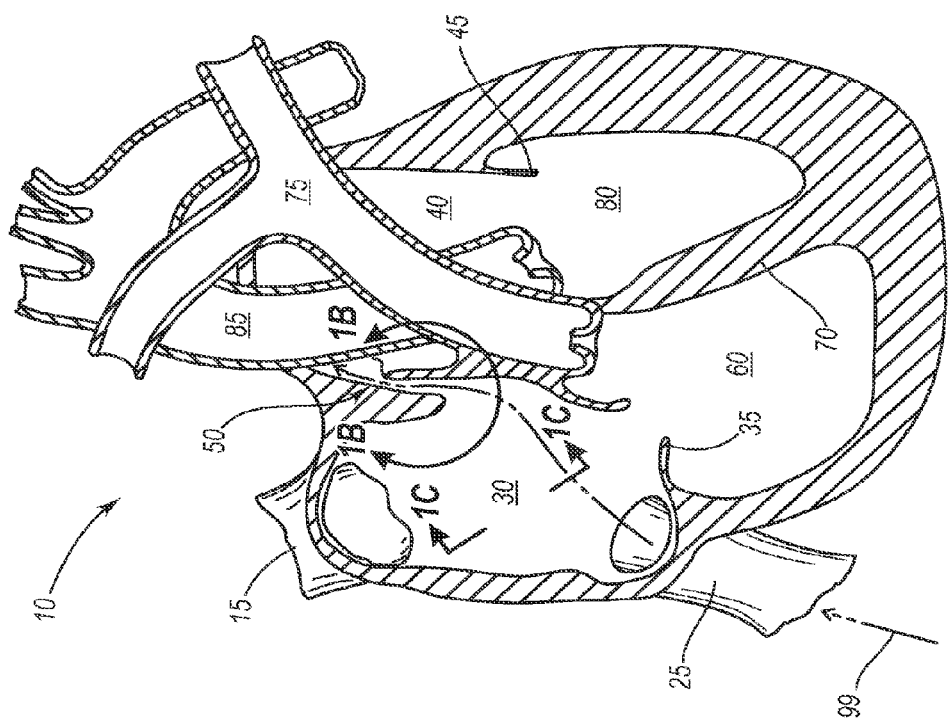

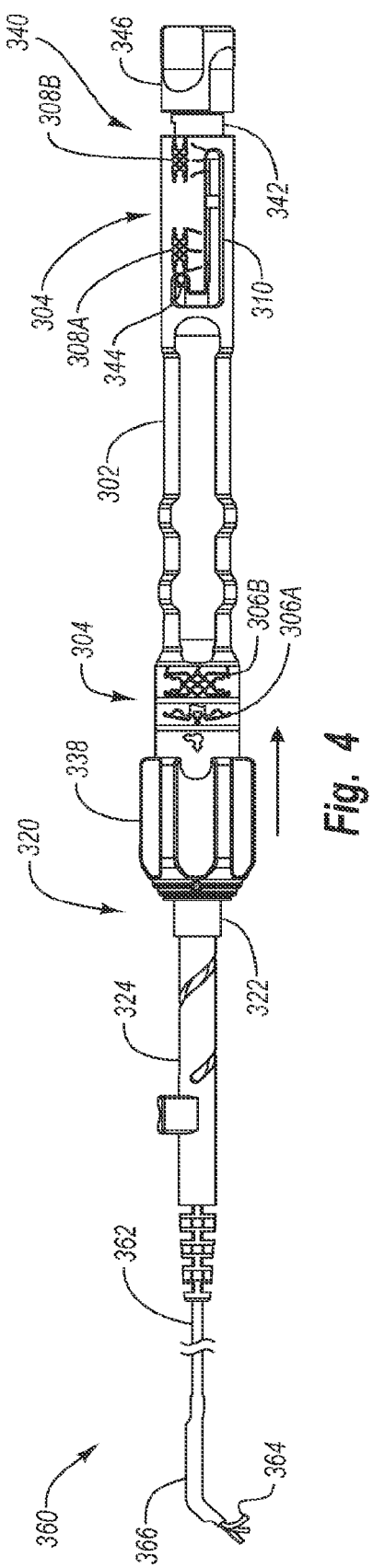
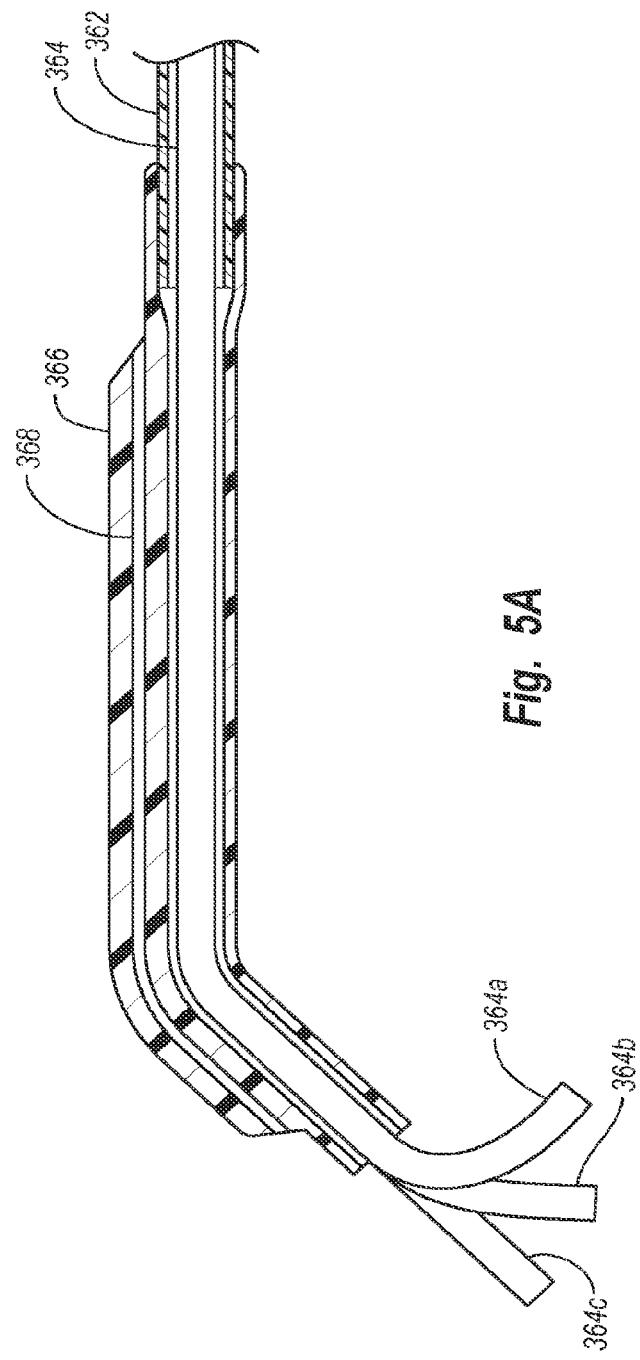
Fig. 4
Fig. 5A

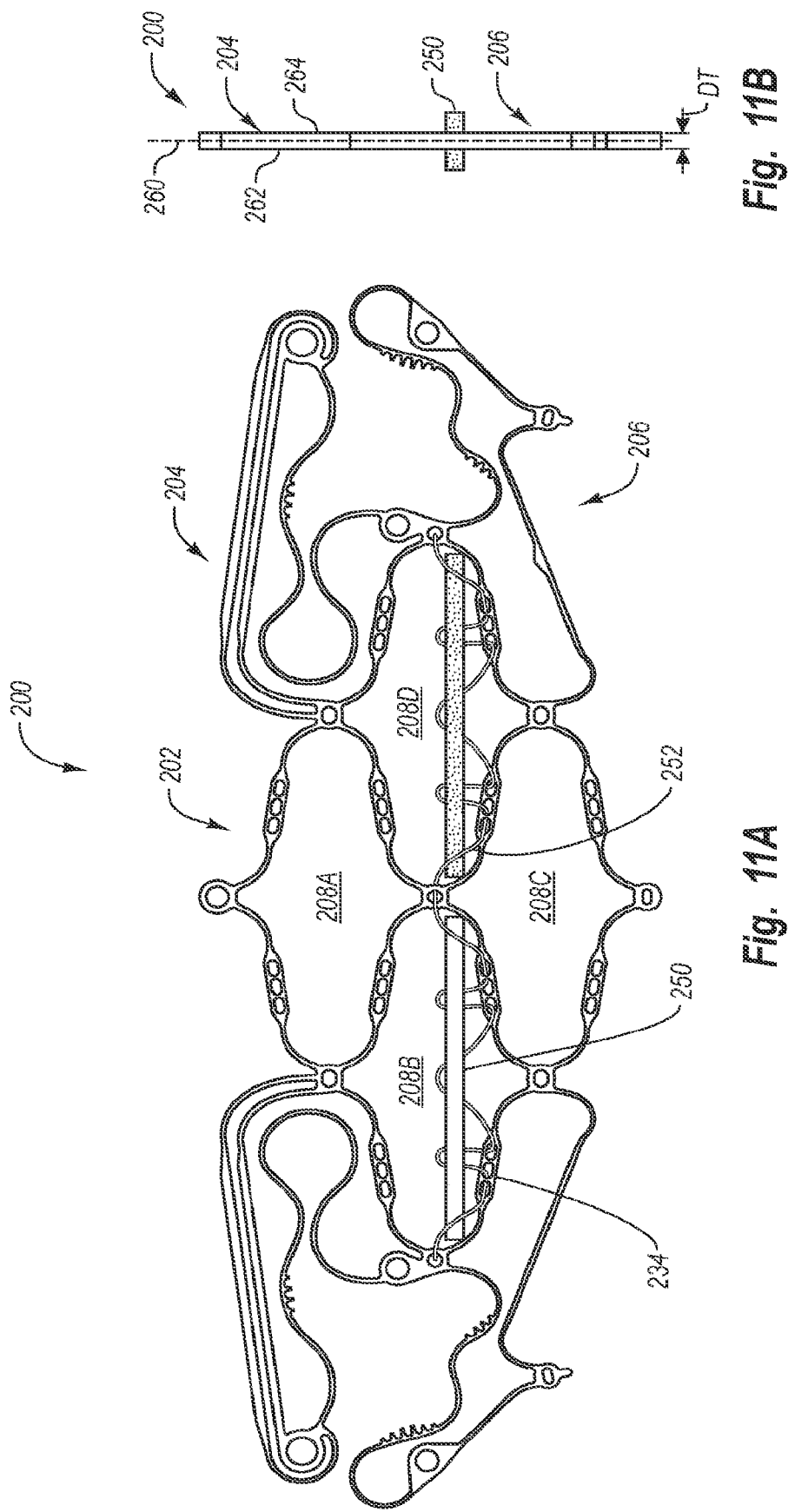

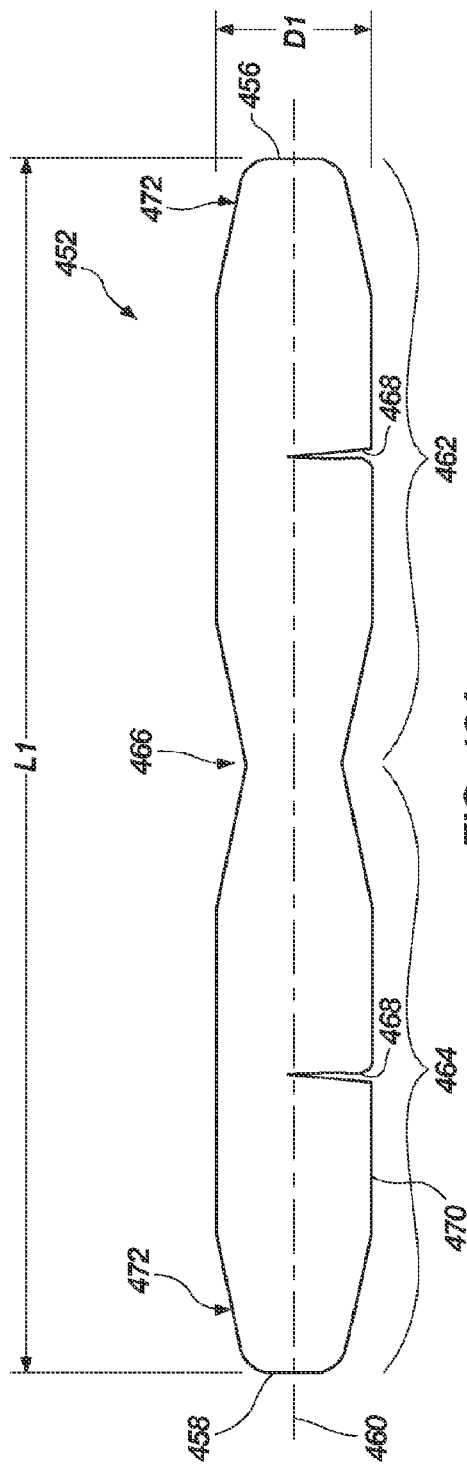
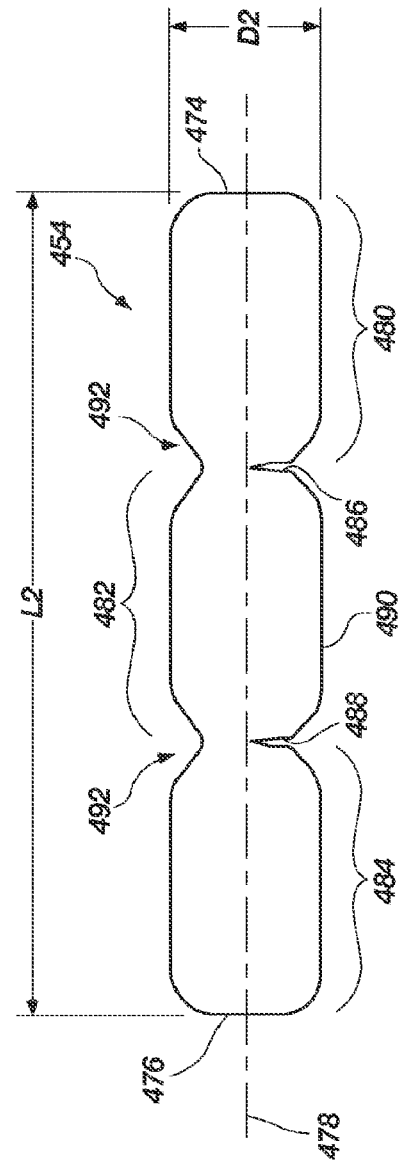

DEVICES FOR REDUCING THE SIZE OF AN INTERNAL TISSUE OPENING

CROSS-REFERENCE TO RELATED APPLICATIONS

The present application is a continuation of U.S. patent application Ser. No. 12/783,498, filed May 19, 2010, now U.S. Pat. No. 8,529,597, which is a continuation-in-part of U.S. patent application Ser. No., 11/836,000 filed Aug. 8, 2007 now U.S. Pat. No. 9,138,208, U.S. patent application Ser. No. 11/836,016 filed Aug. 8, 2007, now U.S. Pat. No. 9,220,487, and U.S. patent application Ser. No. 11/836,123 filed Aug. 8, 2007, now U.S. Pat. No. 8,167,894, each of which claims priority to: U.S. Provisional Application No. 60/821,949 filed Aug. 9, 2006; U.S. Provisional Application No. 60/821,947 filed Aug. 9, 2006; U.S. Provisional Application No. 60/829,507 filed Oct. 13, 2006; U.S. Provisional Application No. 60/866,047 filed Nov. 15, 2006; and U.S. Provisional Application No. 60/942,625 filed Jun. 7, 2007. The disclosures of each of the above-listed applications are hereby incorporated in their entireties by reference herein.

The present application is additionally related to the following U.S. patent applications: U.S. patent application Ser. No. 11/836,037, filed on Aug. 8, 2007, now U.S. Pat. No. 8,979,941; U.S. patent application Ser. No. 11/836,051, filed on Aug. 8, 2007, now U.S. Pat. No. 8,840,655; U.S. patent application Ser. No. 11/836,013, filed on Aug. 8, 2007, now U.S. Pat. No. 8,846,809; U.S. patent application Ser. No. 11/836,026 filed on Aug. 8, 2007, now abandoned; and U.S. application Ser. No. 12/413,334 filed Mar. 27, 2009, now abandoned. The disclosures of each of the above-listed applications are hereby incorporated in their entireties by reference herein.

TECHNICAL FIELD

The present invention relates generally to medical devices and methods of use for treating an internal tissue structure. More particularly, the present invention relates to medical devices, systems, and methods for reducing the size of an internal tissue opening.

BACKGROUND

Physical malformations or defects that are present at birth can be detrimental and even lethal when left uncorrected. A PFO is an example of a cardiac birth defect that can be problematic and even result in death when combined with other factors such as blood clots or other congenital heart defects. A PFO occurs when an opening between the upper two chambers of the heart fail to close after birth.

Some of the problems associated with a PFO can occur when a blood clot travels from the right to the left atria of the heart through the PFO, and lodges in an artery that feeds blood to the brain. A blood clot in the left atrium can be passed through the aorta and travel to the brain or other organs, and cause embolization, stroke, or a heart attack. A PFO can be treated by being closed by a surgical procedure. Additionally, other similar defects (e.g. septal or otherwise) where some tissue needs to be closed in order to function properly can include the general categories of atrial-septal defects ("ASDs"), ventricular-septal defects ("VSD's") and patent ductus arteriosus ("PDA"), and the like.

FIGS. 1A-1C depict various views of a heart having a PFO. The heart 10 is shown in a cross-section view in FIG. 1A. In a normal heart 10, the right atrium 30 receives systemic venous blood from the superior vena cava 15 and the inferior vena cava 25, and then delivers the blood via the tricuspid valve 35 to the right ventricle 60. However, in the depicted heart 10 a septal defect, which is shown as a PFO 50, is present between right atrium 30 and left atrium 40.

The PFO 50 is depicted as an open flap on the septum between the heart's right atrium 30 and left atrium 40. In a normal heart 10, the left atrium 40 receives oxygenated blood from the lungs via pulmonary artery 75, and then delivers the blood to the left ventricle 80 via the mitral valve 45. In a heart 10 having a PFO 50 some systemic venous blood can also pass from the right atrium 30 through the PFO 50 and mixes with the oxygenated blood in left atrium 40, and then is routed to the body from left ventricle 80 via aorta 85.

During fetal development of the heart 10, the interventricular septum 70 divides the right ventricle 60 and left ventricle 80. In contrast, the atrium is only partially partitioned into right and left chambers during normal fetal development, which results in a foramen ovale fluidly connecting the right and left atrial chambers. As shown in FIG. 1B, when the septum primum 52 incompletely fuses with the septum secundum 54 of the atrial wall, the result can be a tunnel 58 depicted as a PFO 50.

FIG. 1C provides a view of the crescent-shaped, overhanging configuration of the septum secundum 54 from within the right atrium 30 in a heart 10 having a PFO 50. The septum secundum 54 is defined by its inferior aspect 55, corresponding with the solid line in FIG. 1C, and its superior aspect 53 represented by the phantom line, which is its attachment location to the septum primum 52. The septum secundum 54 and septum primum 52 blend together at the ends of the septum secundum 54. The anterior end 56a and posterior end 56p are referred to herein as "merger points" for the septum secundum 54 and septum primum 52. The length of the overhang of the septum secundum 54, which is the distance between superior aspect 53 and inferior aspect 55, increases towards the center portion of the septum secundum as shown.

The tunnel 58 between the right atrium 30 and left atrium 40 is defined by portions of the septum primum 52 and septum secundum 54 between the merger points 56a and 56p which have failed to fuse. The tunnel 58 is often at the apex of the septum secundum 54 as shown. When viewed within right atrium 30, the portion of the septum secundum 54 to the left of tunnel 58, which is referred to herein as the posterior portion 57p of the septum secundum, is longer than the portion of the septum secundum 54 to the right of tunnel 58, which is referred to herein as the anterior portion 57a of the septum secundum 54. In addition to being typically longer, the posterior portion 57p also typically has a more gradual taper than the anterior portion 57a as shown. The anterior pocket 59a is the area defined by the overhang of the anterior portion 57a of the septum secundum 54 and the septum primum 52, and it extends from the anterior merger point 56a toward the tunnel 58. Similarly, the posterior pocket 59p is the area defined by the overhang of the posterior portion 57p of septum secundum 54 and the septum primum 52, and it extends from the posterior merger point 56p toward the tunnel 58.

Conventional treatments for PFO, and other related conditions have generally involved invasive surgery, which also presents risks to a patient. Although there are some less invasive treatments for PFO, such treatments have been less efficient at closing the PFO opening than techniques involving invasive surgery.

BRIEF SUMMARY OF THE INVENTION

The invention relates to a medical system, devices and methods of use for reducing the size of an internal tissue opening, such as a Patent Foramen Ovale ("PFO"). In one embodiment of the invention, the medical system can include a closure device and an associated delivery device. The medical system can be configured to enable a practitioner to selectively position and deploy the closure device in an internal tissue opening to approximate, or in other words bring together the tissue of the opening.

In accordance with one embodiment of the present invention, a medical device deployable at least partially within a hole defined in a tissue structure between a first atrium and a second atrium of a heart, the hole defining an axis oriented axially through the hole, is provided. The medical device includes a frame configured to assume a substantially flat configuration oriented substantially parallel to, or extending substantially along, the axis of the hole when in an intended, as-deployed state within the tissue structure. The frame includes a central portion with at least one proximal anchor and at least one distal anchor. The at least one proximal anchor and the at least one distal anchor each configured to be substantially coplanar with the central portion, and the at least one distal anchor configured to extend in the first atrium and the at least one proximal anchor configured to extend in the second atrium. The at least one distal anchor including a plurality of anchor frame segments each extending from the central portion.

In one embodiment, the at least one distal anchor includes a unitary multi-cellular structure. In another embodiment, the plurality of anchor frame segments may include a multi-cellular structure. Further, the plurality of anchor frame segments may include at least three reinforced segments. Furthermore, the plurality of anchor frame segments may include at least two anchor frame segments that extend from the central portion and are substantially parallel to each other along at least a portion along their respective length. In addition, the at least one distal anchor may include two distal anchors each with at least one reinforced segment, the at least one reinforced segment for each of the two distal anchors each extend from a location directly adjacent to each other.

In accordance with another embodiment of the present invention, a medical device deployable at least partially within a hole defined in a tissue structure between a first atrium and a second atrium of a heart, the hole defining an axis oriented axially through the hole, is provided. The medical device includes a frame configured to assume a substantially flat configuration oriented substantially parallel to, or extending substantially along, the axis of the hole when in an intended, as-deployed state within the tissue structure. The frame includes a central portion with at least one proximal anchor and at least one distal anchor. The at least one proximal anchor and the at least one distal anchor each configured to be substantially coplanar with the central portion. The at least one distal anchor configured to extend in the first atrium and the at least one proximal anchor configured to extend in the second atrium. The at least one proximal anchor including one or more engaging members having a wave-crest configuration.

In one embodiment, at least one of the engaging members include a base portion, a peak portion and an edge portion. The base portion extends from the at least one proximal anchor, the peak portion having a surface at a peak of the at least one engaging member, and the edge portion extends from the peak portion. In another embodiment, the peak portion includes an atraumatic surface.

In another embodiment, the medical device includes a tissue growth member configured to be thermally attached to the frame. In still another embodiment, the medical device includes multiple clips extending from portions of the central portion of the frame, the multiple clips configured to attach a tissue growth member to the frame.

In accordance with another embodiment of the present invention, a medical device deployable at least partially within a hole defined in a tissue structure between a first atrium and a second atrium of a heart, the hole defining an axis oriented axially through the hole, is provided. The medical device includes a frame configured to assume a substantially flat configuration oriented substantially parallel to, or extending substantially along, the axis of the hole when in an intended, as-deployed state within the tissue structure. The frame includes a central portion with at least one proximal anchor and at least one distal anchor. The at least one proximal anchor and the at least one distal anchor each configured to be substantially coplanar with the central portion. The at least one distal anchor configured to extend in the first atrium and the at least one proximal anchor configured to extend in the second atrium. The at least one proximal anchor including at least two proximal anchor segments extending from the central portion and extending substantially parallel with each other.

In accordance with another embodiment of the present invention, a medical device deployable at least partially within a hole defined in a tissue structure between a first atrium and a second atrium of a heart, the hole defining an axis oriented axially through the hole, is provided. The medical device includes a frame configured to assume a substantially flat configuration oriented substantially parallel to, or extending substantially along, the axis of the hole when in an intended, as-deployed state within the tissue structure. The frame includes a central portion with at least one proximal anchor and at least one distal anchor. The at least one proximal anchor and the at least one distal anchor each configured to be substantially coplanar with the central portion. The at least one distal anchor configured to extend in the first atrium and the at least one proximal anchor configured to extend in the second atrium. The central portion includes multiple struts to define a multi-cellular structure and at least two of the multiple struts extend substantially parallel and alongside each other.

In one embodiment, the multiple struts are substantially similar in length. In addition, the at least two of the multiple struts may extend along a proximal portion of the frame and may be configured to reinforce the at least one proximal anchor. Further, the at least two of the multiple struts may extend along a distal portion of the frame and may be configured to reinforce the at least one distal anchor.

In another embodiment an expandable medical device is provided that is deployable at least partially within a tissue structure and adjacent a left atrium of a heart. The device comprises a multi-cellular central frame portion configured to self expand from a first, non-tubular orientation to a second, non-tubular orientation, the first orientation being substantially similar to a collapsed orientation within a catheter, the second orientation being substantially similar to an orientation wherein the central frame portion is deployed and operable substantially within the tissue structure and adjacent the left atrium. The central frame portion comprises a plurality of interconnecting central frame support segments defining at least two apertures. At least one of said central frame support segments has a length and a width, the width varying along at least a portion of the length. At least one anchor is linked to said multi-cellular central frame portion.

In yet another embodiment, an expandable medical device is provided wherein the device is deployable at least partially within a hole defined in a tissue structure between a first atrium and a second atrium of a heart, the hole defining an axis oriented axially through the hole. The expandable medical device includes a frame configured to assume a substantially flat configuration oriented substantially parallel to, or extending substantially along, the axis of the hole when in an intended, as-deployed state within the tissue structure. The frame comprises a central portion, at least one proximal anchor and at least one distal anchor. The frame is configured to move between a first orientation and a second orientation. The central portion comprises a plurality of frame segments defining a multi-cellular structure, the at least one proximal anchor and said at least one distal anchor each being configured to extend substantially coplanar with said central portion. The at least one proximal anchor is configured to extend in the first atrium and the at least one distal anchor is configured to extend in the second atrium.

In accordance with a further embodiment, a medical device is provided that is deployable at least partially within a hole defined in a tissue structure, the hole defining an axis oriented axially through the hole. The medical device includes a framework configured to assume a substantially flat configuration oriented substantially parallel to, or extending substantially along, the axis of the hole when in a state for intended deployment within the tissue structure. The framework comprises a central portion and at least one anchor extending from said central portion. The central portion includes central frame segments having a length and a width, wherein the width of at least one of said central frame segments varies along at least a portion of the length of the at least one of said central frame segments in a tapered configuration.

In accordance with yet a further embodiment, a medical device is provided that is deployable at least partially within a hole defined in a tissue structure, the hole defining an axis oriented axially through the hole. The medical device includes a framework configured to assume a substantially flat configuration oriented substantially parallel to, or extending substantially along, the axis of the hole when in a state for intended deployment within the tissue structure, the framework comprises a central portion and at least one anchor extending from said central portion. The central portion includes central frame segments, wherein at least one of the central frame segments includes a longitudinal length dimension and has an aspect ratio of a depth dimension to a lateral width dimension of at least 2 to 1, wherein the depth dimension is defined to extend substantially perpendicular relative to the substantially flat configuration of the framework.

In accordance with another embodiment, an expandable medical device is provided that is deployable at least partially within a hole defined in a tissue structure between a first atrium and a second atrium of a heart, the hole defining an axis oriented axially through the hole. The medical device includes a framework configured to assume a substantially flat configuration oriented substantially parallel to, or extending substantially along, the axis of the hole when in a state for intended deployment within the tissue structure. The framework comprises a central portion, a first proximal anchor, a second proximal anchor and at least one distal anchor extending from said central portion. The first and second proximal anchors are configured to extend in the first atrium and said at least one distal anchor configured to extend in the second atrium. The first proximal anchor and said second proximal anchor each include a plurality of anchor frame segments, wherein at least two of the plurality of anchor frame segments extend substantially parallel to each other along at least a portion of their respective lengths for each of the first proximal anchor and the second proximal anchor.

In yet a further embodiment, an expandable medical device is provided that is deployable at least partially within a hole defined in a tissue structure between a first atrium and a second atrium of a heart, the hole defining an axis oriented axially through the hole. The medical device includes a frame configured to assume a substantially flat configuration oriented substantially parallel to, or extending substantially along, the axis of the hole when in a state for intended deployment within the tissue structure. The frame comprises a central portion and at least one proximal anchor and at least one distal anchor extending from said central portion. The at least one proximal anchor is configured to extend in the first atrium and the at least one distal anchor is configured to extend in the second atrium. A tissue growth member is attached to the frame and comprises: a first elongate tissue growth portion positioned along the central portion of the frame and configured to be positioned in the hole and oriented substantially transverse to the axis of the hole; and a second elongate tissue growth portion positioned proximal to the first elongate tissue growth portion, the second elongate tissue growth portion configured to be oriented substantially transverse to the axis of the hole.

These and other advantages and features and configurations of the present invention will become more fully apparent from the following description and appended claims, or may be learned by the practice of the invention as set forth hereinafter.

BRIEF DESCRIPTION OF THE SEVERAL VIEWS OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIGS. 1A-1C illustrate exemplary views of a heart having a Patent Foramen Ovale;

FIG. 4 illustrates an embodiment of a delivery device according to the present invention;

FIGS. 5A-5C illustrate cross-sectional views of a delivery device according to the present invention;

FIG. 11A illustrates an embodiment of a closure device having an ingrowth material according to the present invention;

FIG. 11B illustrates a side view of the closure device of FIG. 11A;

FIG. 13A illustrates an embodiment of a first ingrowth material for attaching to the frame of a closure device;

FIG. 13B illustrates an embodiment of a second ingrowth material for attaching to the frame of a closure device;

DETAILED DESCRIPTION OF THE INVENTION

The present invention extends to medical systems, methods, and apparatus for reducing the size of an internal tissue opening. By way of explanation, the devices disclosed herein can be used to treat a variety of internal tissue openings, such as a left atrial appendage, paravalvular leaks, PDA's, and VSD's, for example. Although, for purposes of simplicity, frequent reference is made herein to reducing the size of or closing an opening in heart tissue known as Patent Foramen Ovale ("PFO"). Accordingly, it will be understood that references to PFO openings are not limiting of the invention.

In the following description, numerous specific details are set forth to assist in providing an understanding of the present invention. In other instances, aspects of delivery and/or closure devices, or medical devices in general have not been described in particular detail in order to avoid unnecessarily obscuring the present invention. In addition, it is understood that the drawings are diagrammatic and schematic representations of certain embodiments of the invention, and are not limiting of the present invention, nor are they necessarily drawn to scale.

Figure 2:
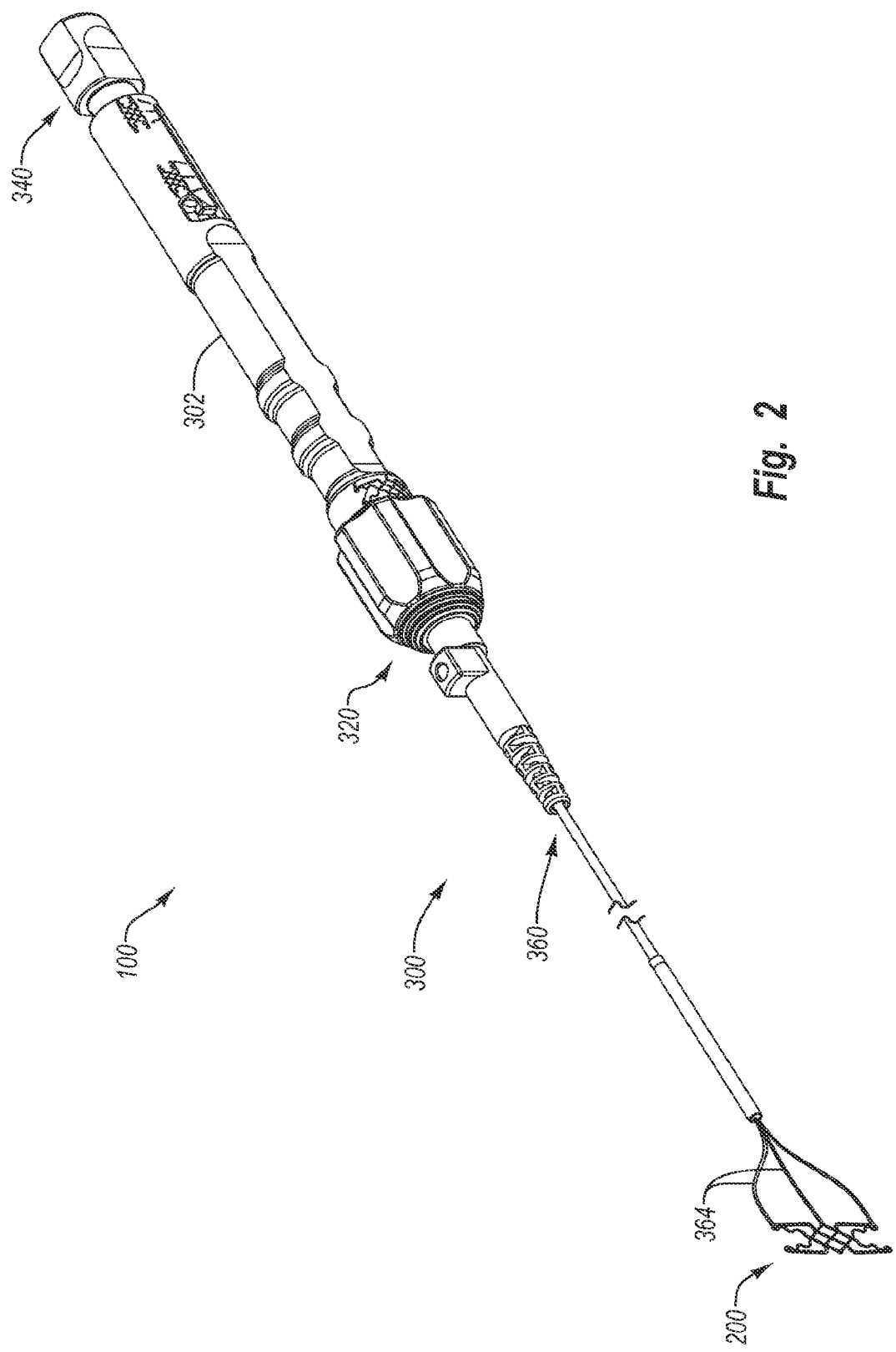
FIG. 2 illustrates a perspective view of an embodiment of a medical system according to the present invention.

FIG. 2 is a perspective view of a medical system 100 configured to facilitate closure of an internal tissue opening according to one embodiment of the present invention. In the illustrated embodiment, the medical system 100 comprises a closure device 200 adapted to reduce the size of the internal tissue opening, and a delivery device 300 adapted to facilitate placement and deployment of the closure device 200 with respect to the internal tissue opening. The medical system 100 of the present invention can provide benefits. For example, the medical system 100 can be configured to be used with different sizes, shapes and types of internal tissue openings. Furthermore, the medical system 100 can provide various safety measures to increase the safety and effectiveness of positioning the closure device 200. In addition, the medical system 100 can be configured to provide distributed lateral force to tissue of the internal tissue opening.

In the illustrated embodiment, delivery device 300 comprises a handle body 302, an actuating assembly 320 operatively associated with handle body 302, a release assembly 340 operatively associated with the handle body 302 and a delivery assembly 360 operatively associated with the actuating assembly 320, the release assembly 340 and the handle body 302. Handle body 302 can be configured to provide a gripping surface for a user. Handle body 302 can be used to position closure device 200, as well as facilitate deployment of the closure device 200 from the delivery assembly 360. Actuating assembly 320 can be moved with respect to handle body 302 to selectively deploy portions of the closure device 200 from the delivery assembly 360, as will be discussed more fully herein below.

Release assembly 340 can be operatively associated with the handle body 302 to enable selective detachment of closure device 200 from the delivery assembly 360. Delivery assembly 360 can house closure device 200 in a non-deployed or constrained orientation, such as illustrated in FIG. 3B for example, and facilitate deployment of closure device 200. Delivery assembly 360 can include one or more tethers 364 linked to the closure device 200 to facilitate selective detachment of the closure device 200 from the delivery device 300.

Figure 3A:
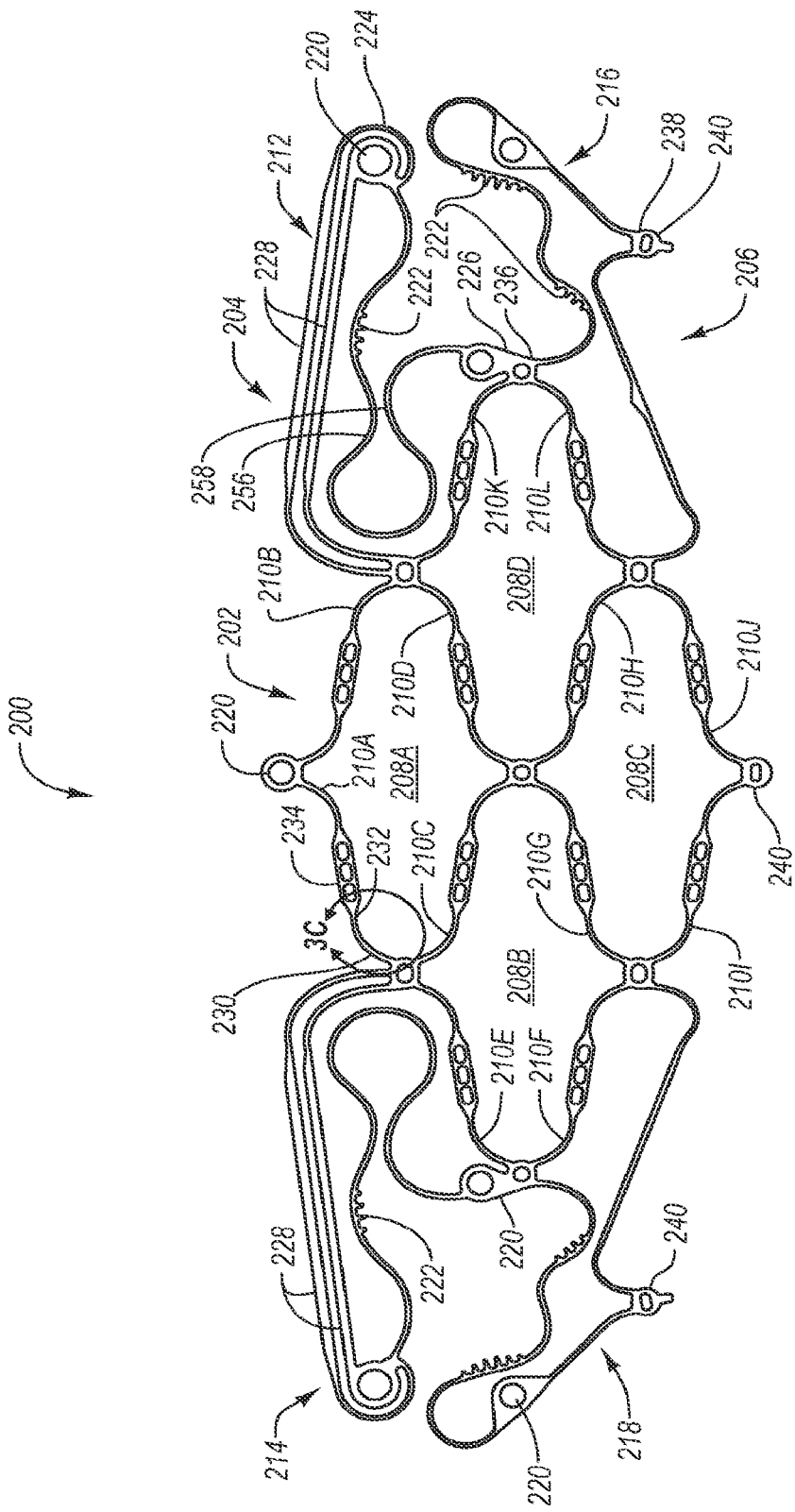
FIG. 3A illustrates an embodiment of a closure device according to the present invention.
Figure 3B:
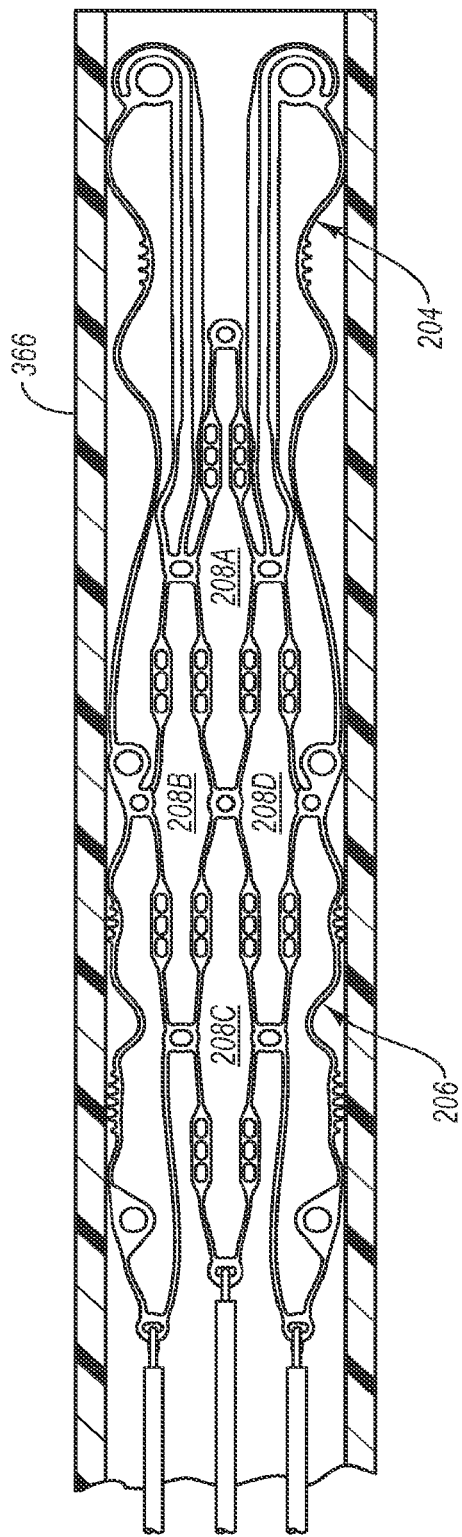
FIG. 3B illustrates an embodiment of a closure device in a non-deployed orientation according to the present invention.

With reference to FIG. 3A, the closure device 200 is illustrated in a fully deployed, expanded, relaxed or non-constrained orientation. According to one embodiment of the invention, the closure device 200 can be configured to reduce the size of an internal tissue opening so as to close the internal tissue opening. In one embodiment, the closure device 200 can reduce the size of an internal tissue opening by approximating, or in other words bringing together tissue of the internal tissue opening, such as tunnel tissue in a PFO. The closure device 200 can approximate tissue by applying lateral force to tissue of the internal tissue opening, as will be discussed more fully herein after. Also, the closure device 200 can be configured to enable a user to estimate the position and/or orientation of the closure device 200 with respect to an internal tissue opening, during and after positioning of the closure device 200 in the internal tissue opening.

According to one embodiment of the invention, the closure device 200 can be a non-tubular stent. The closure device 200 can be configured to assume a substantially flat configuration, or in other words be configured to be substantially planar, such as illustrated in FIGS. 3A and 11B for example. Furthermore, the closure device 200 can be configured to resist movement out of plane, such as plane 260 of FIG. 11B. However, the closure device 200 may bend out of plane when positioned in a tissue opening. In the embodiment shown, the non-tubular configuration of the closure device 200 is maintained both when in constrained within a delivery device as well as when deployed in a tissue structure such as a PFO.

The closure device 200 according to one embodiment of the invention has many advantages. For example, the closure device 200 can be configured to be reliable and compliant. The configuration of the closure device 200 can enable the closure device 200 to be movable between a non-deployed orientation and a deployed orientation without causing failure or plastic deformation of the closure device 200. The closure device 200 can be used to close various types, shapes and sizes of internal tissue openings. Furthermore, the closure device 200 can accommodate for a range of PFO tunnel lengths, for example. Also, the closure device 200 can be partially or fully deployed from or received back into the delivery device 300. Closure device 200 can be configured to substantially conform to the size and shape of a tissue opening. For example, the undulations on the distal and proximal anchors can enable the anchors to substantially, or to a certain degree, conform to the anatomy of a tissue opening.

Generally, the closure device 200 can have a substantially flat aspect having a length and height greater than its depth or depth thickness. For example, in one embodiment, the closure device 200 has an overall length of 22 mm, a height of 7.5 mm and a depth thickness of 0.4 mm. According to one embodiment of the present invention, when the closure device 200 is in the relaxed or completely expanded orientation, as illustrated in FIG. 3A, the distance between the opposing ends of the proximal anchor 218 can be about 22 mm, the distance between the most proximal attachment member 240 of the body portion 202 and the most distal indicator 220 of the body portion 202 can be about 7.5 mm, and the depth thickness, designated as DT in FIG. 11B, of the closure device 200 can be about 0.4 mm.

Furthermore, the majority of segments comprising the closure device 200 can have a thickness or width that is substantially less than the depth thickness of the segments. The closure device 200 can resist out of plane movement due to the size and configuration of the segments. For example, the closure device 200 can be configured to assume a substantially flat configuration in a first plane. The configuration of the segments, for example the segments having a certain depth thickness, can facilitate the closure device 200 resisting movement out of the first plane in a manner similar to an I beam resisting bending in the direction of the web of the beam. The first plane can be plane 260 as illustrated in FIG. 11B.

Also, the closure device 200, according to one embodiment of the invention, can have a unitary construction. For example, the closure device 200 can be cut from a single piece of material, such as cut by a laser, thereby removing the need to assemble or join different segments together. A unitary construction can provide advantages, such as ease of manufacturing and reliability. For example, assembly is not required for a closure device having a unitary construction. Also, a closure device having a unitary construction may not include distinct elements or segments which require joining by joints, thereby reducing a likelihood of failure. The closure device 200 can be made from a super-elastic material, such as a super-elastic metal or a super-elastic polymer. Furthermore, the closure device 200 can be made from NiTiNol, stainless steel alloys, magnesium alloys, and polymers including bio-resorbable polymers.

In some embodiments according to the present invention, the closure device can be formed by utilizing a pressurized stream of water, such as a water jet, to remove material from a piece of material to form the closure device. Furthermore, it is contemplated that the closure device can be formed by utilizing one or more of the following: die casting, chemical etching, photolithography, electrical discharge machining, or other manufacturing techniques. It is contemplated that the closure device can be formed through use of a mill or some other type of device adapted to remove material to form a desired shape.

It will be appreciated by one of ordinary skill in the art in view of the disclosure provided herein that the closure device 200 can comprise multiple segments joined together by a known joining process, such as by an adhesive, by interference fits, crimping, by fasteners, or a weld, or some combination thereof. For example, in one embodiment, the closure device can include multiple segments joined together by various welds to form a closure device according to the present invention. In other embodiments, the segments can be joined together by a plurality of means, such as by the combination of welding, fasteners, and/or adhesives. The segments can be a wire or multiple joined or rolled wires crimped together or joined by a joining process to form the closure device 200.

In the illustrated embodiment, the closure device 200 includes a body portion 202, a first anchor 204 operatively associated with the body portion 202 and a second anchor 206 operatively associated with the body portion 202. The body portion 202 can be configured to facilitate application of lateral force against tissue of an internal tissue opening. Also, the body portion 202 can be configured to enable the closure device 200 be movable between a non-deployed and deployed orientation. For example, the closure device 200 can be configured to be self-expanding from the constrained or non-deployed orientation, as illustrated in FIG. 3B for example, to the relaxed orientation, as illustrated in FIG. 3A. In other words, the closure device 200 can have a preferential orientation, such that movement of the closure device 200 from a first orientation to a second orientation can create internal stresses in the closure device 200. These internal stresses can serve to bias the closure device 200 to the first orientation. For example, in one embodiment, the closure device 200 can have a preferential orientation of the relaxed or fully deployed orientation as illustrated in FIG. 3A. In this embodiment, movement of the closure device 200 to a constrained orientation, such as illustrated in FIG. 3B for example, can create internal stresses in the closure device 200, thereby creating in the closure device 200 a bias to return to the relaxed orientation.

In the illustrated embodiment, body portion 202 includes one or more cells 208 defined by a plurality of segments 210. The body portion 202 can include one or more apertures. In one embodiment, an aperture is defined by the cell 208, or in other words by the plurality of segments 210. In one embodiment, segment 210 can be a strut or a body support segment. Cells 208 can be distinct, or can be at least partially defined by a common segment. For example, cell 208A, as the distal most cell, and cell 208C, as the proximal most cell of body portion 202, are distinct and defined by distinct segments 210 with respect to each other. However, cell 208B is partially defined by a segment 210C which also defines a portion of cell 208A. Similarly, cell 208B is partially defined by a segment 210G which also partially defines cell 208C.

Likewise, cell 208D shares a segment 210D with cell 208A and shares a segment 210H with cell 208C.

Segments 210 can be shaped and configured to have a substantially uniform stress at any given point along a certain length, when the segment 210 is deflected. For example, segment 210A can include a first portion 230 having a width or thickness greater than a second portion 232, wherein the width or thickness decreases from the first portion 230 to the second portion 232, or in other words is tapered, in a manner which provides for substantially uniform stress levels along the certain length. In other embodiments, segments can have a substantially constant width along their length.

Figure 3C:
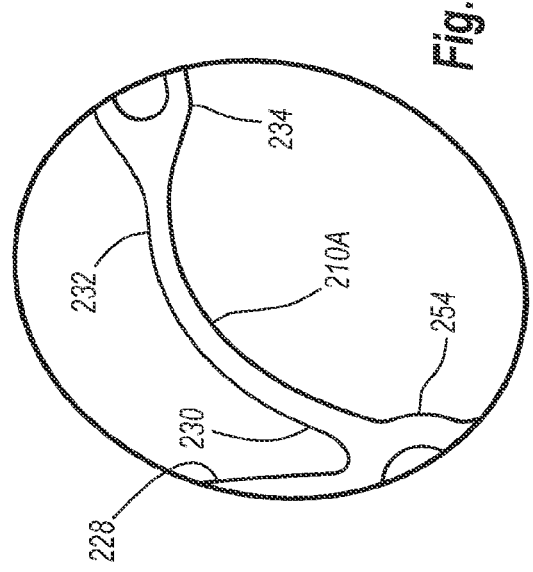
FIG. 3C illustrates a cut-out view of a portion of a closure device according to the present invention.

FIG. 3C is a cut-out view of a portion of the closure device 200, including the first portion 230 and the second portion 232 of segment 210A. In the illustrated embodiment, the width or thickness of the segment 210A varies along the portion of the segment 210A from the location where segment 210A extends from the portion 254 which joins segment 210A to segment 210C to the intermediate portion 234. As the closure device 200 moves between an expanded or otherwise related orientation and a constrained or otherwise collapsed orientation, the segments 210 are deflected, with the highest levels of stress in the segment 210 being concentrated at the joining portion 254 and decreasing towards the intermediate portion 234. The segments 210 can be configured in a manner so as to have a substantially equal stress level along the length of the segment 210 between the joining portion 254 and the intermediate portion 234. The uniform stress level can be accomplished by having the width of the segment 210 vary from the first portion 230 to the second portion 232 in a calculated manner. In one embodiment, the width of the first portion 230 of the segment can be about 0.1 mm and the taper to a width of about 0.05 mm at the second portion 232 of the segment.

In other embodiments, the uniform stress level can be accomplished by utilizing a gradient of material having varying properties. In other embodiments, the segment 210 can have varying widths along its length and comprise a gradient of material sufficient to achieve a substantially uniform stress level between the first portion 230 and the second portion 232 of the segment. In the illustrated embodiment, the first portion is adjacent the joining portion 254 and the second portion is adjacent the intermediate portion 234. In yet additional embodiments, the joints of the interconnecting segments can include a biasing member, such as a spring, thereby enabling the segments to move relative to each other to collapse or expand the closure device 200. Furthermore, the biasing member of the joint can cause the segments to have a preferential orientation with respect to each other.

With continued reference to FIG. 3A, segments 210 can also be configured to have a rectangular cross-section. In other embodiments, segments 210 can have an oval shaped cross section. In yet another embodiment, sections 210 can have a round or rounded cross section. Furthermore, in one embodiment, the ratio, or aspect ratio, of the thickness or width to the depth thickness of the first and second portions 230, 232 can range between at least about 1:2 to about 1:20. In one embodiment, the aspect ratio of the width to the depth thickness of the first portion 230 can be at least 1:2 and the ratio of the width to the depth thickness of the second portion 232 can be at least 1:4. In an alternative embodiment, the aspect ratio of the first portion 230 can be about 1:4 and the aspect ratio of the second portion 232 can be about 1:8. In this manner, the closure device 200 can substantially resist out of plane movement, while allowing in-plane movement during reorientation of various portions of the closure device 200.

Segments 210 can be configured to be compliant. Compliancy of segments 210 can enable cells 208, and thus the body portion 202, to be oriented in various orientations. For example, body portion 202 can be oriented, or in other words moved, between a non-deployed orientation, such as illustrated in FIG. 3B, and a fully deployed orientation, such as illustrated in FIG. 3A. The compliancy of segments 210 can facilitate the accommodation by the closure device 200 of a variety of types, shapes and sizes of internal tissue openings. For example, the size and configuration of the first and second anchors 204, 206 and the body portion 202 can enable the closure device 200 to accommodate varying sizes, shapes and types of internal tissue openings. In one implementation, the first anchor 204 can engage wall tissue of an internal tissue opening and the second anchor 206 can engage only the tunnel tissue of the internal tissue opening to approximate tissue. In an alternative implementation where the internal tissue opening has a shorter tunnel length, the second anchor 206 can engage the tunnel tissue and an opposing wall of the internal tissue opening to approximate tissue.

Segments 210 can include an intermediate portion 234 configured to facilitate securement of ingrowth materials to the closure device 200, or can be used as an indicator 220 to facilitate estimation of the position of the closure device 200 with respect to an internal tissue opening. Furthermore, intermediate portion 234 can be configured to facilitate measuring of a characteristic of an internal tissue opening. In one embodiment, intermediate portion 234 can include one or more apertures. The apertures can be configured to receive a securing element, such as a thread, therethrough to facilitate securing an ingrowth material to the closure device 200. Intermediate portion 234 can be configured to be stiffer or more rigid than first portion 230, second portion 232, or both. A stiffer intermediate portion 234 can increase the reliability of segments 210.

In another embodiment, the intermediate portion 234 can include an indicator 220, such as a dense metallic rivet or concentration of dense material, for use in estimating the orientation and/or position of the closure device 200. Understanding of the orientation and/or position of the closure device 200 can facilitate estimating a physical characteristic of an internal tissue opening and/or the relative position of the closure device 200 with respect to the internal tissue opening. For example, if the distance between the indicators 220 is known, a practitioner can estimate a physical characteristic, such as the opening or tunnel width, by determining the new distance between the indicators 220 when the closure device 200 is positioned in the tissue opening. Similarly, indicators 220 can be positioned on the first and second anchors 04, 206. The indicators 220 can be configured and arranged on the closure device 200 such that when the first anchor 204 is deployed the indicators 220 are substantially aligned. In this manner, a practitioner can estimate whether the first anchor 204 has fully deployed.

In some cases, it may be difficult to view the closure device 200 in the event the closure device 200 is at a skewed angle with respect to the viewing plane, such as a fluoroscope. When the closure device 200 is skewed in this manner, it can be difficult to determine accurately the distance of interest. However, when various distances between indicators is known, a user can use the known distances to calculate the distances of interest by using geometry.

In one embodiment, segments 210 along a similar or common lateral plane can have substantially equal lengths. Substantially equal lengths of segments 210 in this manner can enable body portion 202 to be moved between the non-deployed and deployed orientation without failure of the segments 210. For example, in one embodiment, segments 210A and 210B have substantially the same length, segments 210E, 210C, 210D, and 210K have substantially the same length, segments 210F, 210G, 210H and 210L have substantially the same length, and segments 210I and 210J have substantially the same length. In this configuration, body portion 202 can be collapsed or oriented into the non-deployed orientation, as illustrated in FIG. 3B, without causing damage to the body portion 202 of closure device.

The closure device 200 can be configured to have a preferential orientation of the fully deployed orientation as illustrated in FIG. 3A. As the closure device 200 is deployed from the delivery device 300, the configuration of closure device 200 can cause the closure device 200 to preferentially move toward the fully deployed orientation. Thus, as the closure device 200 is deployed in an internal tissue opening, the preferential orientation of the closure device 200 can cause the closure device 200 to apply lateral force to the tissue of the internal tissue opening. In other words, the body portion 202, first anchor 204 and the second anchor 206 are deflected by an applied force in order to reorient the closure device 200 from the fully deployed orientation to a non-deployed orientation, for example. In this manner, the closure device 200, because of the deflection of the body portion 202, first anchor 204 and the second anchor 206, will have tendency to return to the fully deployed orientation. When the closure device 200 is positioned in an internal tissue opening, the deflected body portion 202, first anchor 204 and the second anchor 206 can have a tendency to apply a lateral force to tissue of the opening as the closure device 200 attempts to return to the fully deployed orientation.

Body portion 202 can be operatively associated with the first anchor 204 and the second anchor 206. First and second anchors 204, 206 can be configured to move between a deployed and non-deployed orientation. First and second anchors 204, 206 can be configured to apply lateral force to tissue of an internal tissue opening, and to engage and/or contact a portion of wall tissue and/or tunnel tissue of an internal tissue opening. In one embodiment, the first anchor 204 can be a left atrial anchor, and the second anchor 206 can be a right atrial anchor.

In the illustrated embodiment, the first anchor 204 can include a first anchor segment 212 and an opposing second anchor segment 214. Likewise, the second anchor 206 can include a first anchor member 216 and an opposing second anchor member 218. The first anchor segment 212 can be configured to move relative to the second anchor segment 214. Likewise, the first anchor member 216 can be configured to move relative to the second anchor member 218. In this manner, the closure device 200 can accommodate for a variety of types, shapes and sizes of internal tissue openings. The first anchor segment 212 and the second anchor segment 214 can be configured to be substantially similar in size, shape and configuration. As such, reference to the configuration and/or function of one of the first or second anchor segments can apply to the other anchor segment. In one embodiment of the invention, the first anchor 204 and/or the second anchor 206 can include one or more undulations. The undulations can facilitate reorienting or movement of the anchors with respect to the body portion 202, for example, from a deployed to a non-deployed configuration. Furthermore, the undulations can facilitate the anchor substantially conforming to the anatomy of the tissue opening.

The first anchor segment 212 can include a distal end 224 and a proximal end 226. The first anchor segment 212 can be defined by various segments and can include reinforced segments 228 and one or more engaging members 222. For example, in the illustrated embodiment, the first anchor segment 212 is at least partially defined by segment 210K of cell 208D. The engaging members 222 can be microposts or tines configured to contact and/or engage tissue. The engaging members 222 can include a sharp tip or can be blunt. The engaging members 222 can be configured to provide a degree of surface texture in order to increase engagement of the first anchor 204 with tissue.

The first anchor segment 212 can be configured to be moved between a non-deployed orientation, as illustrated in FIG. 3B, and a fully deployed orientation, as illustrated in FIG. 3A. The first anchor segment 212 can be configured such that the distance from the proximal end 226 to the distal end 224 of the segment which includes the engaging members 222 is substantially equal to the distance from the proximal end 226 to the distal end 224 of the segment which includes the reinforced segments 228 and segment 210K. The second anchor segment 214 can be configured similar to the first anchor segment 212.

First anchor segment 212 can be configured to define a closed periphery. For example, first anchor segment 212 can include the reinforced segment 228 extending from the body portion 202 to the segment having the engaging members 222 which is connected to segments 210K, 210L to define a closed periphery with segment 210K. Furthermore, two reinforced segments 228 can extend from the joining portion 254 of the body portion 202 and join together near the distal end 224 of the first anchor 204. As such, there are multiple anchor portions extending from the body portion 202. In this manner, anchors of the present invention are reinforced to provide greater rigidity and strength to facilitate stabilization and maintenance of the closure device 200 within a tissue structure.

First anchor member 216 can include a distal end 236 and a proximal end 238. The first anchor member 216 can be defined by various segments and can include one or more engaging members 222. For example, in the illustrated embodiment, the first anchor member 216 is at least partially defined by segment 210L of cell 208D. The engaging members 222 can be microposts or tines configured to contact and/or engage tissue. The engaging members 222 can include a sharp tip or can be blunt. The engaging members 222 can be configured to provide a degree of surface texture to increase engagement of the second anchor 206 with tissue.

It will be understood by one of ordinary skill in the art in view of the disclosure provided herein that the engaging members 222 can vary in size and shape, and can be positioned at various locations on the closure device 200. In alternative embodiments, one or more engaging members can extend out of plane of the closure device so as to contact tissue which is perpendicular, for example, to the substantially flat plane, such as plane 260 of FIG. 11B, of the closure device 200.

The first anchor member 216 can be configured to be moved between a non-deployed orientation, as illustrated in FIG. 3B, and a fully deployed orientation, as illustrated in FIG. 3A. The first anchor member 216 can be configured such that the distance from the proximal end 238 to the distal end 236 of the segment which includes the engaging members 222 is substantially equal to the distance from the proximal end 238 to the distal end 236 of the segment which includes segment 210L. In this manner, first anchor member 216 can be detachably coupled to the delivery device 300 when in a non-deployed orientation inside the delivery device 300 as illustrated in FIG. 3B. The second anchor member 218 can be configured similar to the first anchor member 216.

The first anchor segment 212 can also include a first portion 256 and a second portion 258 configured to facilitate engagement of the internal tissue opening. For example, first anchor segment 212 can be configured to include one or more undulations causing the first portion 256 to be positioned in close proximity with second portion 258. In this manner, as tissue is positioned between the first and second portions 256, 258, the configuration of the first anchor segment 212 can engage, or to some degree, pinch the tissue therebetween to facilitate maintenance of the position of the closure device 200 with respect to the tissue opening.

The closure device 200 can also include attachment members 240 for use in detachably linking the closure device 200 to the delivery device 300, as will be discussed more fully herein after. The attachment members 240 can include an aperture 242 for use in facilitating the linking of the closure device 200 to the delivery device 300.

FIG. 3B illustrates the closure device 200 in a non-deployed or constrained orientation. The configuration of the body portion 202, and the first and second anchors 204, 206 enables the closure device 200 be reoriented from the fully deployed and preferential orientation, as illustrated in FIG. 3A, to the non-deployed or collapsed orientation as illustrated. In the collapsed or non-deployed orientation, the first anchor 204 extends distally and the second anchor 206 extends proximally, with the attachment members 240 being the proximal most portions of the second anchor 206 and the body portion 202.

In the illustrated embodiment, the closure device 200 is positioned inside of a delivery portion 366 of the delivery device 300. The configuration of the closure device 200 can cause portions of the closure device to apply force to the wall of the delivery portion 366 due to the preferential orientation of the closure device 200. The closure device 200 is configured to be received into and deployable from the delivery portion 366.

FIG. 4 illustrates one embodiment of the delivery device 300. In the illustrated embodiment, the delivery assembly 360 includes a catheter 362 having a delivery portion 366, and a plurality of tethers 364 at least partially housed by the catheter 362. The tethers 364 can be configured to facilitate selective detachment of the closure device 200 from the delivery device 300. The delivery portion 366 can be configured to receive the closure device 200 therein. The catheter 362 can be coupled to the actuating assembly 320, such that movement of the actuating assembly 320 can cause movement of the catheter 362.

In the illustrated embodiment, the actuating assembly 320 includes a first member 322 operatively associated with the handle body 302, a second member 324 operatively associated with the first member 322 and the handle body 302, and a knob 338 linked to the first member 322. The actuating assembly 320 can be utilized by a user to selectively deploy the closure device 200 from the catheter 362.

The handle body 302 can include indicia 304 to enable a user to estimate the degree of deployment of the closure device 200 from the delivery device 300, as well as predict detachment of the closure device 200 from the delivery device 300. For example, indicia 304 can include deployment indicia 306 and release indicia 308. Deployment indicia 306 can be utilized to enable a user to estimate the degree of deployment of the closure device 200 from the catheter 362, and the release indicia 308 can be utilized to predict the detachment of the closure device 200 from the delivery device 300. The handle body 302 can also include a release pin groove 310. The release pin groove 310 can be operatively associated with the release assembly 340 to facilitate the selective detachment of the closure device 200 from the tethers 364.

According to one embodiment of the invention, the release assembly 340 can include a biasing member 342 operatively associated with the handle body 302 to facilitate detachment of the closure device 200. A release knob 346 can be provided to manipulate the position of biasing member 342 in order to release or detach the closure device 200. In one embodiment, the release knob 346 is coupled to the biasing member 342, such that movement of the release knob 346 can cause movement of the biasing member 342. The biasing member 342 can include a release pin 344 configured to be received in, influenced by and movable in the release pin groove 310. In this manner, release pin groove 310 can restrict, and thereby influence the movement of the biasing member 342 with respect to the handle body 302.

Figure 10A:
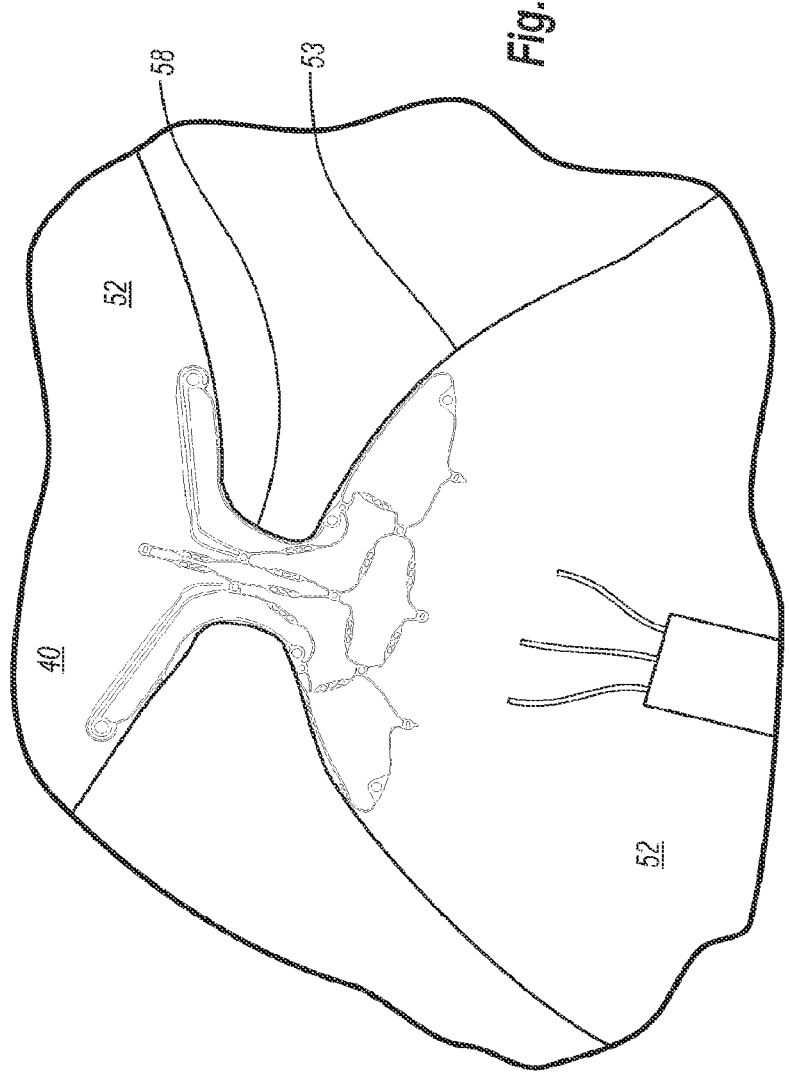
FIG. 10A illustrates an embodiment of a closure device positioned in an internal tissue opening.
Figure 10B:
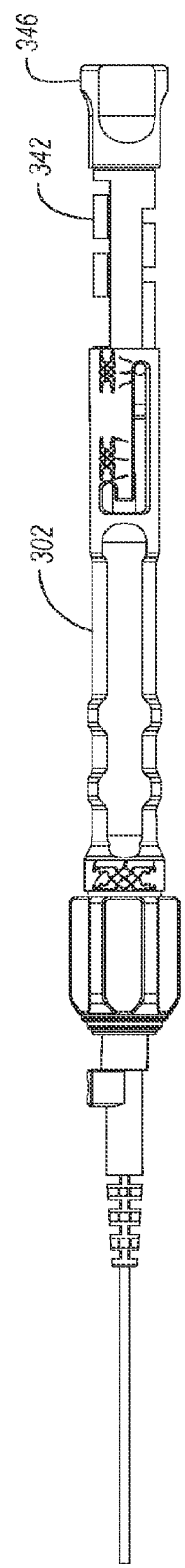
FIG. 10B illustrates an embodiment of a delivery device in an orientation corresponding to the deployed and detached closure device of FIG. 10A.

The biasing member 342 is configured to interact with the handle body 302 such that when the release pin 344 is positioned in a terminating portion of the release pin groove 310, as illustrated in FIG. 4, the biasing member 342 is biased in the proximal direction with respect to the handle body 302. In this manner, the release pin 344 can be moved from the terminating portion of the release pin groove 310, as illustrated in FIG. 4, to the opposing terminating portion of the release pin groove 310 adjacent the release indicia 308B by applying force to the biasing member 342 through the release knob 346 in the distal direction, rotating the release knob 346 and then moving the release knob 346 in the proximal direction to release the closure device 200, as illustrated in FIG. 10B.

FIG. 5A is a cross-sectional view of the distal end of the catheter 362. In the illustrated embodiment, the catheter 362 includes a delivery portion 366 for use in positioning the catheter 362. The catheter 362 can be made from a resilient material having sufficient axial stiffness to allow a practitioner to position the catheter 362 with respect to an internal tissue opening, and sufficient rotational stiffness to allow a practitioner to rotate the catheter 362 by rotating the handle body 302.

In one embodiment, the catheter 362 comprises a braided polyimide. In other embodiments, the catheter 362 can be made from a material having a sufficient axial stiffness, such as a braid reinforced polymer, axially reinforced polymer, metal reinforced polymer, carbon reinforced polymer, or some other type of axially stiff material. The delivery portion 366 can be made from a thermoplastic elastomer, such as PEBAX®. In other embodiments, the delivery portion or tip portion 366 can be made from a material having sufficient flexible properties, such as a polymeric material. In other embodiments, the delivery portion 366 can include a combination of materials, such as metallic materials and polymeric materials.

The delivery portion 366 can define a lumen 368 to facilitate placement of the catheter 362. For example, a guide wire can be received in the lumen 368 to guide the catheter 362 to a desired location. In this manner, the closure device 200 can be located proximate to the internal tissue opening in a quick and efficient manner. Furthermore, the delivery portion 366 can be shaped, such as including a bend, in order to facilitate placement of the delivery portion 366 through a PFO, for example. In one embodiment of the invention, the catheter 362 can be considered a rapid exchange catheter wherein the delivery or tip portion 366 enables a guide wire to be linked to the catheter 362 in a quick and efficient manner for placement of the catheter 362.

The catheter 362 and delivery portion 366 can be configured to at least partially house tethers 364 in a lumen which is distinct and separate from lumen 368. For example, lumen 368 can be in a spaced apart, non-coaxial arrangement from the lumen which houses tethers 364, such that a guide wire can be received through lumen 368 without being introduced into the lumen or space in which the tethers 364 are housed. In this manner, a user can introduce a guide wire into the lumen 368 at the distal end of the catheter 362, rather than the lumen which at least partially houses the tethers 364 which would require the guide wire to be introduced into the lumen at the proximal end of the catheter 362. In alternative embodiments, the lumen 368 configured to receive the guide wire therein can be positioned inside the lumen which houses the tethers 364. In this embodiment, lumen 368 would include an opening and an exit at the distal end of the catheter 362 in order to facilitate the quick placement of a guide wire through the lumen 368.

In one embodiment, catheter 362 can include a rounded cross-section and the delivery portion 366 can include a rectangular cross-section. The rectangular cross-section of the delivery portion 366 can facilitate proper deployment of the closure device 200 from the delivery device 300, as well as facilitate the closure device 200 being reintroduced back into the delivery portion 366. The rectangular cross-section of the delivery portion 366 can be sized to orient the tethers 364 next to each other in a linear fashion. In this manner, the likelihood that the tethers 364 cross each other upon reintroduction of the closure device 200 into the delivery portion 366 can be reduced.

In one embodiment of the invention, tethers 364 includes three tethers 364A-C, each tether 364 being sized and configured to attach to and/or accommodate therein an attachment member 240 of the closure device 200. One example of a tether is a line or hollow tube coupled to the handle body 302. The tether 364 can comprise a flexible, hollow shaft having sufficient stiffness such that as actuating assembly 320 moves the catheter 362 proximally with respect to the handle body 302, the closure device 200 is forced out of the delivery portion 366. Likewise, the tether 364 can be configured to pull the closure device 200 back into the delivery portion 366 as the actuating assembly 320 is moved distally with respect to the handle body 302.

Figure 7:
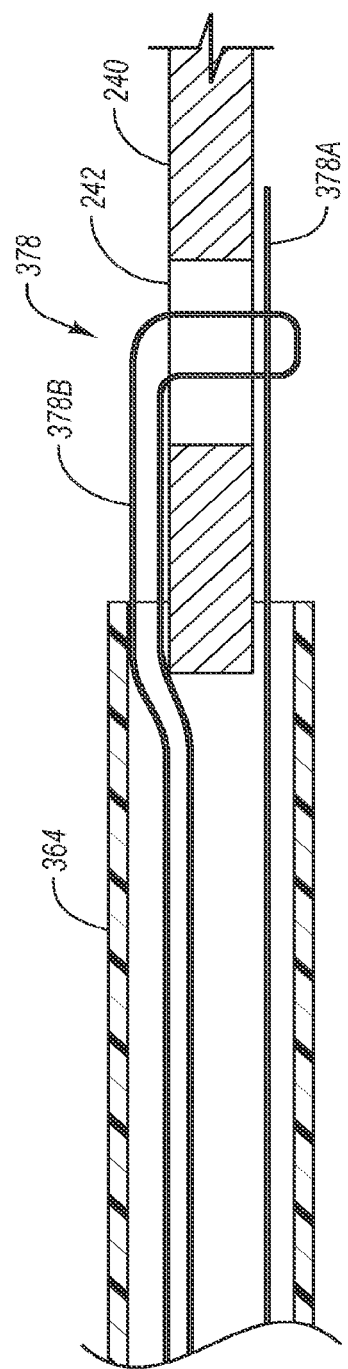
FIG. 7 illustrates an embodiment of a coupling system according to the present invention.

In one embodiment, the tether 364 can be a coil of stainless steel covered by a heatshrunk tubing to give the coil a degree of tensile strength and rigidity. In an alternative embodiment, the tether 364 can be a polymeric tube. In yet an additional embodiment, the tether 364 can be a combination of polymeric materials and metallic materials. In some embodiments, an additional heatshrunk tubing covers a proximal segment of the three tethers 364A-C. The heatshrunk covering can increase the column strength of the tether 364, which can enable the tethers 364 to assist with deployment and reintroduction of the closure device 200 from and into the delivery portion 366. The tethers 364 can have a distal tip configured to correspond to the shape and size of the attachment members 240 of the closure device, such that the attachment member 240 can be received into the distal tip of the tether 364, as illustrated in FIG. 7.

Tethers 364 can be made from a material having sufficient flexibility to substantially prevent distortion or otherwise influence the orientation of the closure device 200 when the closure device is deployed from the catheter 362, yet have sufficient axial strength to facilitate deployment of the closure device 200 when the catheter 362 is moved proximally with respect to the closure device 200. The tethers 364 can have a lumen extending therethrough of sufficient size and configuration to enable a plurality of wires 378 to be housed and movable therein.

Figure 5B:
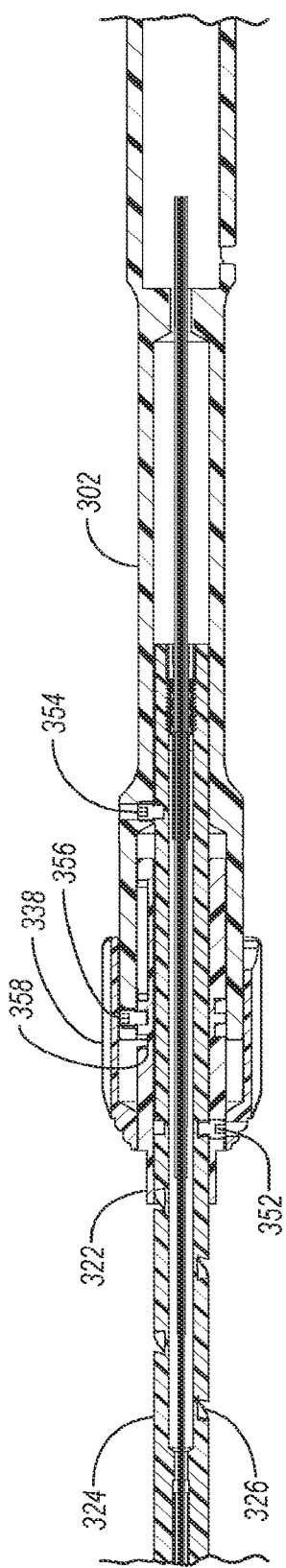
Figure 5C:
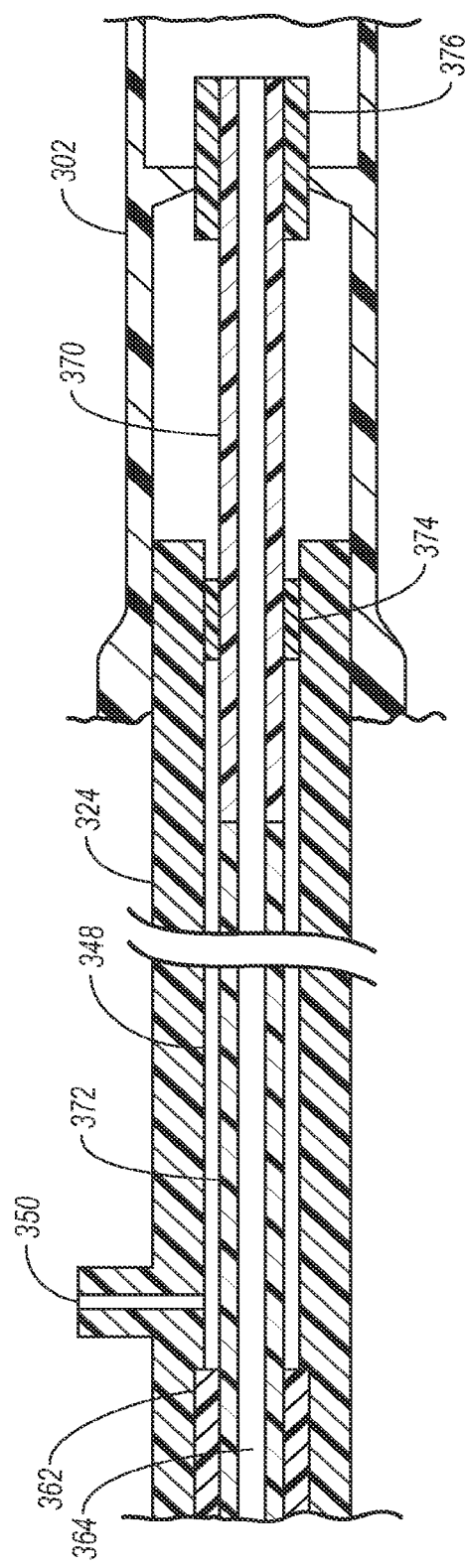

FIGS. 5B-5C are cross-sectional views illustrating the delivery assembly 360 in association with the actuating assembly 320. However, for simplicity, FIG. 5B does not include the biasing member 342 and associated release knob 346, and FIG. 5C illustrates details about the interaction between the delivery assembly 360 and the actuating assembly 320 without illustrating the first member 322 and details about the handle body 302 and the second member 324. In the illustrated embodiment, the proximal end of the catheter 362 is coupled to the distal end of the second member 324. In this manner, movement of the second member 324 can cause a corresponding movement in the catheter 362. For example, as the second member 324 moves proximally with respect to the handle body 302, so also does the catheter 362 move proximally with respect to the handle body 302.

According to one embodiment of the invention, the tethers 364 can extend from the delivery portion 366, through the catheter 362 and the second member 324 and are coupled to the handle body 302. The tethers 364 can be coupled to the handle body 302 by, for example, an intermediate member 376. The tethers 364 can be covered with a first and second housing 370, 372 to provide a degree of rigidity to the portions of the tethers 364 located inside of the handle body 302 and the second member 324. For example, in one embodiment, the first housing 370 comprises a rigid, hollow, metal rod configured to house the three tethers 364A-C therein. The first housing 370 can extend from the intermediate member 376, which facilitates securement of the tethers 364 to the handle body 302, and terminate at some point beyond the handle body 302.

In the illustrated embodiment, the second housing 372 can extend from the distal end of the first housing 370 and extend into the catheter 362. The second housing 372 can comprise a resilient material configured to resist axial stretching while allowing a degree of bending. In one embodiment, the second housing 372 comprises a coil of metal, such as stainless steel, configured to resist axial stretching, yet allow a degree of bending. The second housing 372 can allow a practitioner to bend a portion of the catheter 362, if needed, in order to manipulate delivery device 300 for placement of the closure device 200. A seal 374 can be provided between the first housing 372 and the second member 324 in order to reduce or substantially prevent bodily fluid, which may have entered the catheter 362, from entering the handle body 302 or otherwise inappropriately being expelled from the delivery device 300.

In the illustrated embodiment, the second member 324 can comprise an elongate shaft defining an axial lumen 348 and a lumen 350 in fluid communication therewith. Lumen 350 can be configured to couple to a medical device for removal of fluid from the delivery device 300. The axial lumen 348 can be sized to accommodate and allow movement of the tethers 362, the first housing 370 and the second housing 372 therein. The second member 324 can include a guide 326. The guide 326 can be configured to cooperate with a first pin 352 and a second pin 354 to influence movement of the second member 324 with respect to the handle body 302, as will be discussed more fully herein below.

In the illustrated embodiment, the first member 322 comprises a hollow elongate tube sized and configured to enable the second member 324 to be received into and moveable within the first member 322. The first member 322 can be operatively associated with the handle body 302 and the second member 324 to facilitate deployment of the closure device 200. For example, the first member 322 is linked to the handle body 302 by a third pin 356. The third pin 356 is received in a guide 358 of the first member 322. The guide 358 is configured to interact with the third pin 356 in order to influence the movement of the first member 322 with respect to the handle body 302.

The first pin 352 can link the first member 322 to the second member 324. When the first pin 352 links the first member 322 to the second member 324, the second pin 354 links the handle body 302 to the second member 324, and the third pin 356 links the handle body 302 to the second member 322, movement of the first member 322 can selectively deploy the closure device 200 from the delivery portion 366.

Figure 6:
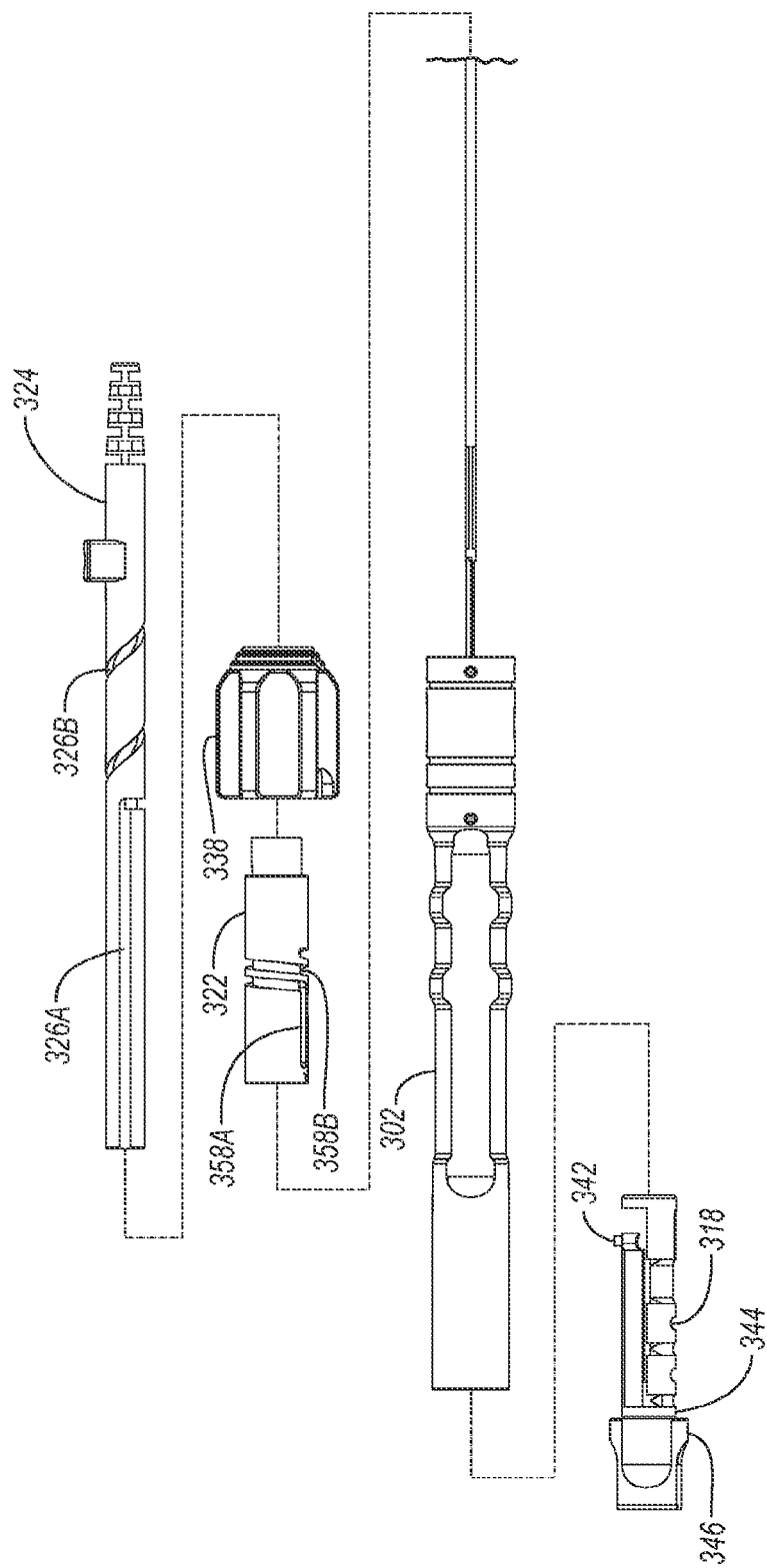
FIG. 6 illustrates an exploded view of a delivery device according to the present invention.

With reference to FIGS. 5A-C and 6, the association between the first member 322, the second member 324, the handle body 302 and the biasing member 342 will be discussed. FIG. 6 is an exploded view of the actuating assembly 320 and the release assembly 340. In the illustrated embodiment, the second member 324 is received into the first member 322, and the first member 322 is received into the knob 338 and the handle body 302, as illustrated in FIGS. 4 and 5B-5C.

According to one embodiment of the invention, the second member 324 can include a guide 326 having a first portion 326a and a second portion 326b, which guide 326 can be defined by a slot formed on the outer surface of the second member 324. In the illustrated embodiment, the first portion 326a is straight and extends along at least a portion of the length of the first member 324 and joins with the second portion 326b of the guide 326. The second portion 326b can include a helical groove or slot that begins with and is contiguous with the first portion 326a and extends distally therefrom.

The guide 326 of the second member 324 is configured to interact with the handle body 302 and the first member 322 to selectively retract the catheter 362 in order to deploy the closure device 200. For example, the first portion 326a of the guide 326 is configured to interact with the second pin 354, which is secured into the handle body 302 by means of threads and extend into the first portion 326a of the guide 326. In this manner, the second member 324 can move laterally with respect to the handle body 302. Thus, rotation of the handle body 302 can translate to rotation of the second member 324, and thus, the catheter 362 and the delivery portion 366.

The second portion 326b of the guide 326 is configured to interact with the first pin 352, which is secured to the first member 322 by means of threads and extends into the second portion 326b of the guide 326. In this manner, as the first member 322 is rotated, the first pin 352 will interact with the second portion 326b to move the second member 324 in the proximal direction. As the second member 324 is moved in the proximal direction with respect to the handle body 302, the catheter 362 moves proximally with respect to the handle body 302 thereby exposing or deploying the closure device 200 from the delivery portion 366.

In the illustrated embodiment, the first member 322 can include a guide 358 defined by a slot or groove formed in the outer surface of the first member 322. In the illustrated embodiment, the guide 358 can include a first portion 358a connected to a second portion 358b. The first portion 358a of guide 358 can be straight and extend along at least a portion of the length of the first member 322, and then join and be contiguous with the second portion 358b. The second portion 358b of the guide 358 can be a helical groove that wraps around at least a portion of the outer surface of the first member 322 and extends along at least a portion of the length of the first member 322.

As described previously, the third pin 356, which is secured to the handle body 302 by means of threads, can extend into the guide 358 in order to influence movement of the first member 322 with respect to the handle body 302. For example, as the third pin 356 is positioned in the most proximal portion of the first portion 358a, the closure device 200 is completely received into and enclosed by the delivery portion 366. As the first member 322 is moved in the proximal direction as illustrated by the arrow in FIG. 4, the third pin 356 moves in the first portion 358a of the guide 358 to deploy the first anchor 204 of the closure device 200 from the delivery portion 366.

The length of the first portion 358a can correspond with the distance that the first member 322, and thus the catheter 362, must move in order to deploy the first anchor 204 of the closure device 200 from the delivery portion 366. For example, a practitioner can move the knob 338, which is coupled to the first member 322, in the proximal direction. Movement of the knob 338 in the proximal direction can cause the third pin 356 to move linearly in the first portion 358a of the guide 358. In this manner, the second member 324 can move correspondingly with the first member 322 because of the first pin 352, which links the first member 322 to the second member 324. As the third pin 356 is positioned in the location of the guide 358 where the first portion 358a meets with the second portion 358b, the first member 322 can be rotated in order to selectively deploy the remaining portions of the closure device 200 from the delivery portion 366 of the delivery device 300.

As the first member 322 is rotated, the third pin 356 is positioned in the second portion 358b to influence movement of the first member 322 with respect to the handle body 302, and the first pin 352, which is coupled to the first member 322, interacts with the second portion 326b of the guide 326 to move the second member 324 in the proximal direction with respect to the handle body 302. Movement of the second member 324 in the proximal direction in this manner can cause further deployment of the closure device 200 from the delivery portion 366. As will be appreciated, the knob 338 can be coupled to the first member 322 to facilitate and enable movement of the first member 322 with respect to the handle body 302.

The dual movement required to deploy the closure device 200 can provide some efficiency and safety advantages. For example, a practitioner can move the knob 338 in a first direction (i.e., proximally in a linear fashion) to deploy the first anchor 204 from the delivery portion 366. Thereafter, the practitioner can move the handle body 302 to position the first anchor 204 against the wall tissue of an internal tissue opening, such as against the left atrial wall of a heart, for example. Once the first anchor 204 is positioned against the wall, the practitioner can move the knob 338 in a second direction (i.e., rotate the knob) to further deploy the closure device 200 from the delivery portion 366. The dual movement enables a user to predict the deployment of the closure device 200 to reduce the risk of premature deployment of the closure device.

It will be understood by one of ordinary skill in the art in view of the disclosure provided herein that other means of controlling movement of one member with respect to the other, such as the first member with respect to the second member, can be utilized without departing from the scope and spirit of the invention. For example, a structure configured to substantially restrict or control movement of the first element with respect to the second element and/or handle body can be utilized. In one embodiment, the structure can include a cam and a follower. In an alternative embodiment, the structure can include a slider.

The release assembly 340 can be configured to be received in the proximal end of the handle body 302. The release assembly 340 can be configured to provide additional safety features for the practitioner and patient by reducing the risk of premature detachment of the closure device 200 before it is positioned appropriately in an internal tissue opening. For example, a practitioner using the medical system 100 of the present invention can manipulate the actuating assembly 320 to deploy the closure device 200 for positioning in an internal tissue opening. In order to deploy a first portion of the closure device 200, a user can move the knob 338, and thus the first member 322, in the proximal direction with a first movement, which is a linear movement, then deploy the remaining portions of the closure device 200 by a rotational movement. Once the closure device 200 is deployed, the practitioner can be required to move their hands in order to utilize the release assembly 340 to release the closure device 200 from the delivery device 300.

In the illustrated embodiment the release assembly 340 can include a release knob 346 coupled to a biasing member 342, which is received into the proximal end of the handle body 302. The biasing member 342 can be configured to include a plurality of slots 318 configured and arranged to act similar to a spring. The slots 318 can be configured and arranged in the biasing member 342 to enable at least a portion of the biasing member 342 to be compressed. Compression of the biasing member 342 can cause the release pin 344 to move toward the distal end of the biasing member 342.

The biasing member 342 can be configured such that when biasing member 342 is positioned in the handle body 302, the biasing member 342 naturally tends to maintain its position with the release pin 344 in the release pin groove 310 as illustrated in FIG. 4. As force is applied to the release knob 346 in the distal direction (i.e., compress the biasing member 342), the release pin 344 can be moved out of a terminating portion of the release pin groove 310 and rotated and moved into a proximal terminating portion of the release pin groove 310 to release the closure device 200 from the delivery device 300.

The closure device 200 is released from the delivery device 300 by moving a plurality of wires 378 which are housed by a tether 364 and coupled to the biasing member 342. Illustrated in FIG. 7 is a cross-sectional view of attachment member 240 of the closure device 200 received into a tether 364 and coupled by first and second wires 378a, 378b. In the illustrated embodiment, a second wire 378b can extend through and out of the tether 364 and form a loop. The loop can extend through an aperture 242 of the attachment member 240 of the closure device 200. With the loop of second wire 378b positioned through the aperture 242 of the attachment member 240, a first wire 378a, which extends through and out of the tether 364, can extend through the loop of the second wire 378b to form a locking feature. When the first wire 378a extends sufficiently through the loop of the second wire 378b, the closure device 200 can remain coupled to the delivery device 300 until the first wire 378a is pulled through the loop of the second wire 378b, and the second wire 378b is pulled out of the aperture 242 of the attachment member 240.

The first wire 378a and the second wire 378b can be attached at their proximal ends to the biasing member 342. In this manner, movement of the biasing member 342 in the proximal direction can cause movement of the wires 378 also in the proximal direction. In one embodiment, the wires 378 can be coupled to the biasing member 342 such that movement of the biasing member 342 will cause the first wire 378a to move a distance sufficient to be removed from the loop of second wire 378b before the second wire 378b is moved by the biasing member 342. The wire 378 can comprise a metallic wire, such as a NiTiNol wire. The wire 378 can also include a stainless steel wire or some other type of metal or stiff polymer. The wires 378 can be made from a material having a sufficient tensile strength to secure the closure device 200 to the tethers 364 without causing the wires 378 to fail or substantially deform. In one embodiment of the invention, the wire 378B can include a stainless steal wire and wire 378A can include a NiTiNol wire.

Other types and configurations of biasing members can be utilized without departing from the scope and spirit of the invention. For example, in one embodiment, the release assembly can include a rotating member coupled to the securing elements. In this embodiment, rotation of the rotating member can cause the securing elements to wind around the rotating member thereby causing the distal ends of the securing elements to move proximally with respect to the handle body.

Figure 8A:
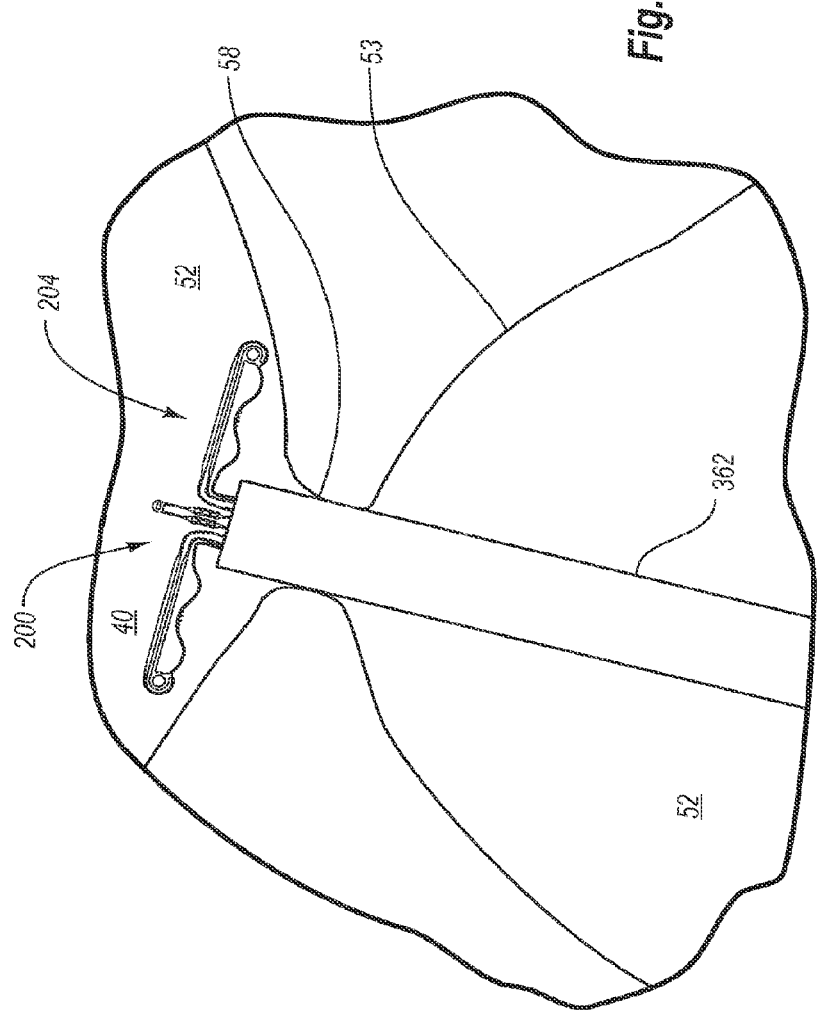
FIG. 8A illustrates an embodiment of a closure device being partially deployed in an internal tissue opening.
Figure 8B:
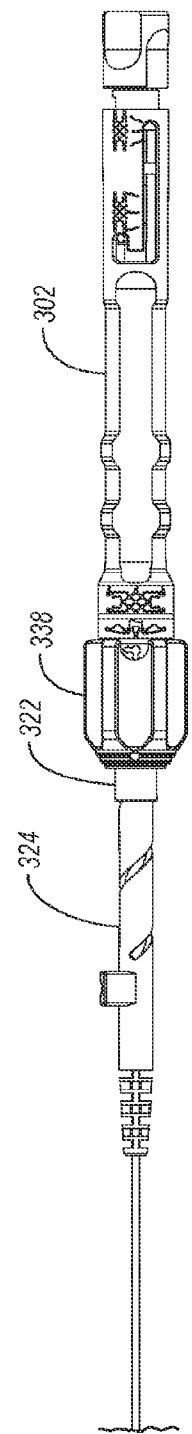
FIG. 8B illustrates an embodiment of a delivery device in an orientation corresponding to the partially deployed closure device of FIG. 8A.
Figure 9:
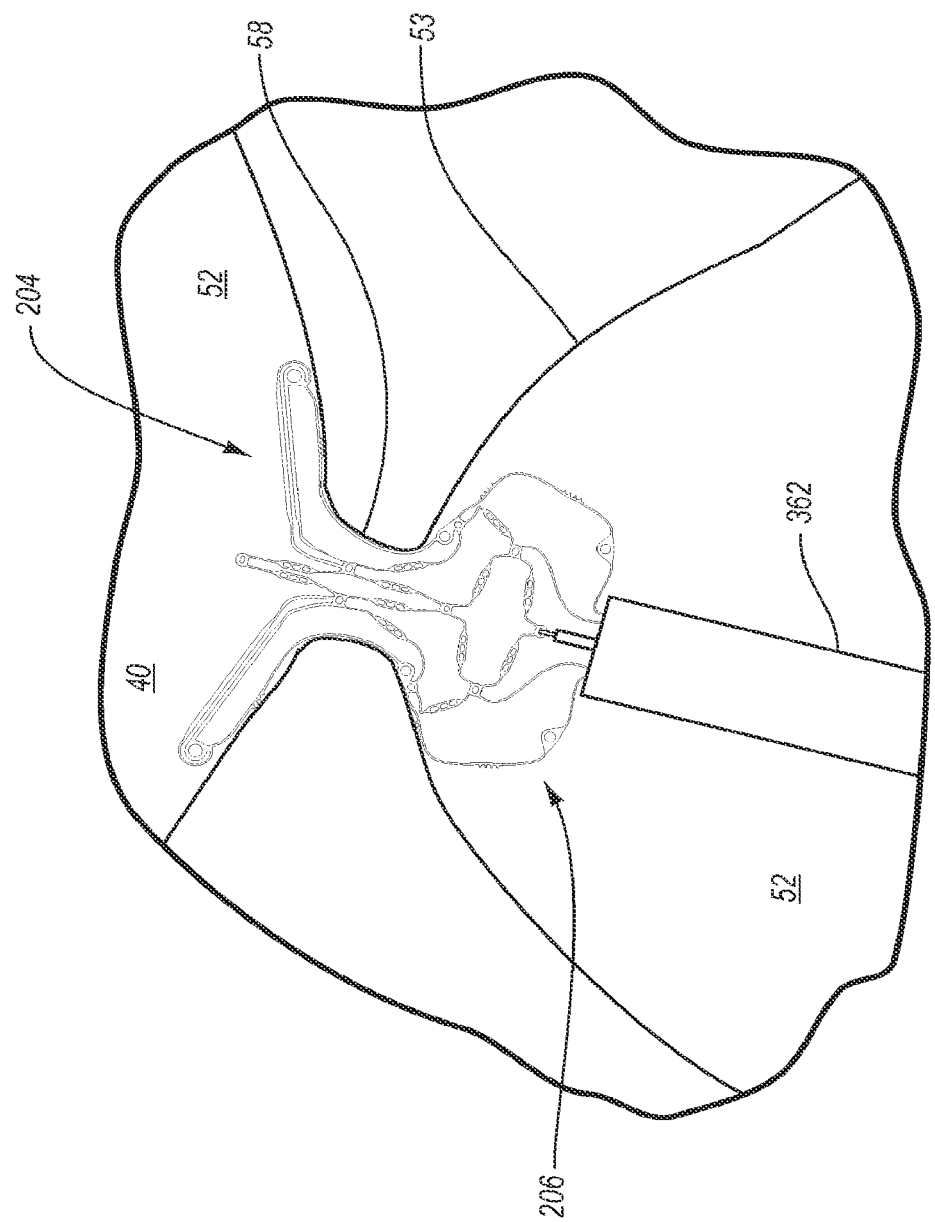
FIG. 9 illustrates an embodiment of a partially deployed closure device according to the present invention.

The method of use of the medical system 100 will now be described with reference to a particular internal tissue opening, namely a PFO. FIG. 8a illustrates the positioning of the catheter 362 through the tunnel 58 of a PFO with the first anchor 204 of the closure device 200 deployed. The medical system 100 is utilized to close an internal tissue opening by positioning the catheter 362 through an internal tissue opening and moving the first member 322 by a first movement (i.e., linearly) in the proximal direction to deploy the first anchor 204 of the closure device 200. After the first anchor 204 of the closure device 200 is deployed, the delivery device 300 can be moved in the proximal direction in order to seat the first anchor 204 against the wall of the tissue opening or otherwise engage the wall of the internal tissue opening, as illustrated in FIG. 9. This can be done by moving the handle body 302 in the proximal direction.

After the first anchor 204 has been positioned against the wall of the internal tissue opening, the knob 338, and thus the first member 322, can moved by a second movement, or in other words, rotated to deploy additional portions of the closure device 200 as illustrated in FIG. 9. After the closure device 200 has been fully deployed and conforms to the anatomy of the internal tissue opening, the release assembly 340 can be actuated to selectively detach the delivery device 300 from the closure device 200 as illustrated in FIGS. 10a and 10b.

The release assembly 340 can be actuated by moving the biasing member 342 distally with respect to the handle body 302, then rotating the biasing member with respect to the handle body 302, and then moved proximally with respect to the handle body 302. In this manner, closure device 200 substantially conforms to the anatomy of the internal tissue opening. As noted previously, the configuration of the closure device 200 is such that when positioned in the internal tissue opening as illustrated, the members of the closure device 200 apply lateral force to the tissue of the internal tissue opening, such as the tunnel 58 of the PFO, to approximate tissue of the PFO for closure.

FIG. 11A illustrates one embodiment of a closure device 200 that can include a member 250, such as an ingrowth material. The member 250 can be configured to induce tissue growth. The member 250 can be fixed to the closure device 200 by means of a securing element, such as a thread 252. For example, the thread 252 can extend through the member 250 and through the apertures in the intermediate portions 234 in order to secure the member 250 to the closure device 200. In other embodiments, the member 250 can be secured to the closure device 220 by a known securing means, such as by an adhesive, a heat weld, or some other known or hereafter developed means for securement.

The member 250 and the thread 252 can include a bio-resorbable material, such as polylactide or polyglycolide or collagen. The member 250 can be sized and configured to enable the closure device 200 to be deployed from and received into the delivery portion 366 of the delivery device 300. Furthermore, the member 250 can be configured to interact with tissue of the internal tissue opening to stimulate growth of tissue for closure of the internal tissue opening. For example, the member 250 can interact with the tunnel tissue 58 of a PFO in order to stimulate growth of tissue in the PFO tunnel 58.

The member 250 can be any suitable material which can or tends to promote tissue growth. Examples of such material can include a polymeric material, or a woven material, such as a woven metallic or biological material. In one embodiment, the member 250 can be a piece of foam. In alternative embodiments, the member 250 can be a piece of yarn, fabric or string, or some combination thereof. Other tissue growth promoting members can include a coating disposed on the closure device 200. In other embodiments, the member 250 can be a piece of foam, braided material such as a piece of yarn or string, or fabric which has a coating disposed thereon.

The member 250 can include materials such as a piece of polyurethane or some other biocompatible polymer, including bio-resorbable polymers. The member 250 can also include Dacron or polymeric threaded material which have been woven or knitted, or formed into compressed, non-woven fabrics. The member 250 can also include a metallic material, such as a NiTiNol, stainless steal or some other biocompatible alloy or bio-resorbable metal, such as magnesium alloy, or some combination thereof. In one embodiment, the member 250 comprises a metallic wire.

FIG. 11B illustrates a side view of the closure device 200, and illustrates one example of the closure device having a substantially flat configuration. In the illustrated embodiment, the closure device 200 can include a depth or depth thickness designated as DT, and a plane 260 extending perpendicular into and out of the plane of the page. In this embodiment, the member 250 can extend beyond at least a first edge 262 of the closure device 200. Furthermore, the member 250 can extend beyond both the first edge 262 and a second edge 264 of the closure device 200. In this manner, member 250 can contact tissue adjacent the closure device 200 to promote tissue growth in the tissue opening.

The member 250 can be sized and configured to extend beyond at least the first edge 262 of the closure device 200 a sufficient distance to contact tissue of the tissue opening. In one embodiment, the member 250 can extend beyond at least the first edge 262 a sufficient distance to contact tissue adjacent the first edge 262, thereby causing the end of the member 250 which is in contact with the tissue to deflect or bend. In this manner, more surface area of the member 250 can be in contact with tissue to thereby facilitate an increase in tissue growth. In other embodiments, the member 250 can extend beyond both the first edge 262 and the second edge 264 a sufficient distance to cause both ends of the member 250 to bend, which can result in more surface area contacting the tissue. In one embodiment, the member 250 can extend between at least 0.5 mm and 5 mm beyond the first edge 262. In another embodiment, the member 250 can extend between at least 0.5 mm and 5 mm beyond the first edge 262, and can extend between at least 0.5 mm and 5 mm beyond the second edge 264. Furthermore, the member 250 can have a thickness of between at least 0.25 mm and 2 mm.

In addition, in some embodiments the member 250 can be configured to decrease the size of a remaining void in the tissue opening after the closure device 200 has been positioned in the tissue opening. Member 250 extending beyond the first edge 262 of the closure device 200 is an example of the member 250 extending substantially out of plane of the substantially flat configuration.

Figure 12B:
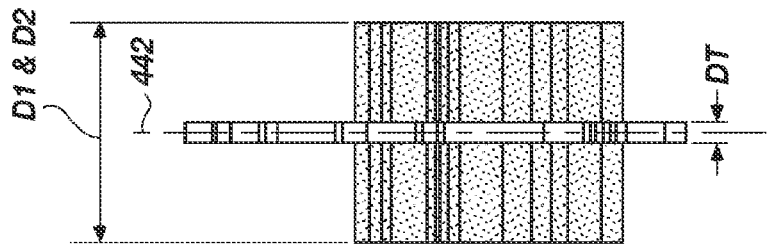
FIG. 12B illustrates a side view of the closure device of FIG. 12A.
Figure 12A:
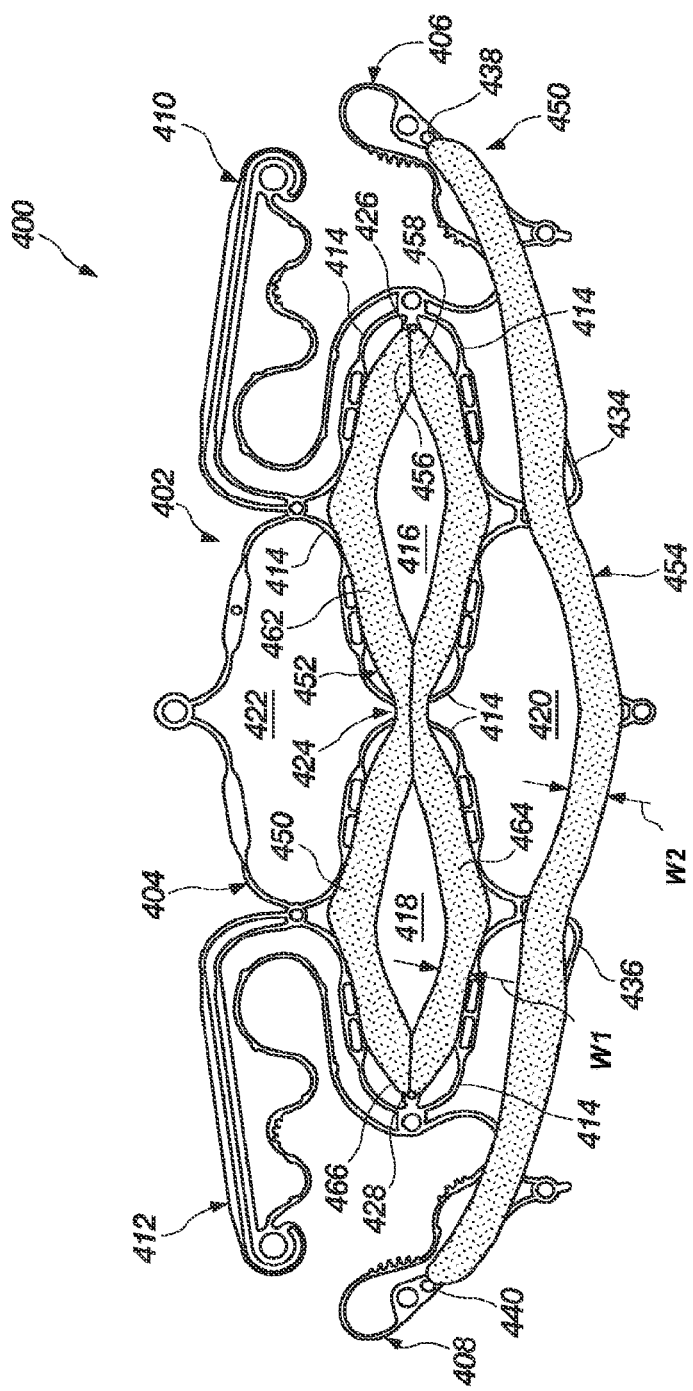
FIG. 12A illustrates another embodiment of a closure device having a first ingrowth material and a second ingrowth material.

FIG. 12A illustrates another embodiment of a closure device 400 with a tissue growth member 450 or in-growth material. The closure device 400 includes a frame 402, similar to frames depicted in the previous embodiments. As previously described, the frame 402 includes a central portion 404 with first and second proximal anchors 406 and 408 and first and second distal anchors 410 and 412, the proximal anchors extending from a proximal portion of the central portion 404 and the distal anchors extending from a distal portion of the central portion 404 of the frame 402. The central portion 404 may include multiple struts 414 that define a multi-cellular structure. In particular, the multiple struts 414 may define four cells in the presently described embodiment: a first central cell 416, a second central cell 418, a proximal cell 420 and a distal cell 422, each of the multiple struts 414 collectively defining the central portion 404 of the frame 402. As previously set forth, the frame 402 is a generally flat plane 442 (FIG. 12B) or substantially planar (or may be described as including or exhibiting a substantially flat configuration) when in an expanded configuration and generally resists movement out of such substantially planar or flat configuration. Further, the frame 402 may remain in a substantially flat configuration when constricted within the tip portion of the catheter (not shown) or at any other deployment stage.

The tissue growth member 450 may include a first member 452 and a second member 454, the first member 452 being separate and distinct from the second member 454. The tissue growth member 450 may be attached to the frame 402 by, for example, stitching or sewing, similar to that illustrated in the previous embodiment. In one embodiment, the tissue growth member 450 is configured to be positioned to extend along struts 414 in the central portion 404 of the frame 402 and may include portions extending along a portion of the first and second proximal anchors 406 and 408 of the frame 402.

The tissue growth member 450 is configured to be biocompatible and porous for inducing tissue growth therein. In one embodiment, the tissue growth member 450 may be foam. In another embodiment, the tissue growth member 450 may be polyurethane. In still another embodiment, the tissue growth member 450 may be polyurethane foam and, more specifically, may be reticulated polyurethane foam. Such foam may also be non-reticulated polyurethane foam. Other materials and structures may also be employed, as set forth in the previous embodiments. Further, the tissue growth member can be formed, for example, from a large stock of foam and shaped as desired utilizing die cutting techniques as known in the art.

With reference to FIG. 13A, the first member 452 is depicted as being an elongated member extending between a first end 456 and a second end 458 and defining a longitudinal axis 460 therethrough. Further, the first member 452 can include a first portion 462 and a second portion 464 defining a mid portion 466 therebetween. Each of the first portion 462 and second portion 464 also can include a slot 468 that extends from a bottom edge 470 of the first member to about the longitudinal axis 460. Further, the first member 452 can include tapered portions 472 that taper toward the first end 456 and the second end 458 as well as the mid portion 466 of the first member 452.

With respect to FIGS. 12A and 13A, the first portion 462 of the first member 452 is sized and configured to be positioned along the distal struts within the first central cell 416 and the second central cell 418, the slot 468 configured to receive a center portion 424 of the frame 402. The first end 456 can be attached to a first eyelet 426 of the frame 402 and the mid portion 466 can be attached to a second eyelet 428 of the frame 402. Similarly, the second portion 464 of the first member 452 is sized and configured to be positioned along proximal struts within the first central cell 416 and the second central cell 418 with the slot 468 of the second portion 464 disposed over or receiving the center portion 424 of the frame 402. Also, similar to the first portion 462, the second end 458 can be attached to the first eyelet 426 and the mid portion 466 can be attached to the second eyelet 428. In this manner, the first member 452 is attached within the first and second central cells 416 and 418 of the frame 402 with the second portion 464 being positioned proximal the first portion 462 of the first member 452. In addition, the second portion 464 of the first member 452 is positioned and oriented within the central portion 404 of the frame 402 to substantially mirror an orientation and position of the first portion 462 of the first member 452.

Further, once the first member 452 is positioned within the central portion 404 of the frame 402, the tapered portions 472 are adjacent the lateral sides of the frame 402 with the intention to correspond or mimic the shape of a PFO tunnel. Essentially, it is desired to have more of the tissue growth member 450 at intermediate portions of the first portion 462 and second portion 464 of the first member to fill any potential gap to, thereby, occlude the PFO tunnel. In this manner, the first member 452 may extend a greater dimension from the frame 402 at a middle portion of the central portion 404 of the frame 402 than at or adjacent the lateral edges of the central portion 404 of the frame 402.

With respect to FIG. 13B, the second member 454 is depicted as being an elongated member extending between a first end 474 and a second end 476 with a longitudinal axis 478 extending therethrough. The second member 454 can include a first portion 480, a second portion 482 and a third portion 484, the second portion 482 being between the first and third portions 480 and 484. The second member 454 can include slots extending from a bottom edge 490 to a central region (e.g., to about the longitudinal axis 478 as depicted in FIG. 13B). The slots can include a first slot 486 defined between the first portion 480 and the second portion 482 and a second slot 488 defined between the second portion 482 and the third portion 484. The second member 454 can also include tapered portions 492 defined adjacently between the first and second portions 480 and 482 and the second and third portions 482 and 484. The first end 474 and second end 476 can define beveled or rounded edges to limit potential abrasion between the second member 454 and, for example, the tip portion of the catheter (not shown) when being constricted therein.

Referring now to FIGS. 12A and 13B, the second member 454 may be sized and configured to be attached to a proximal portion of the frame 402 and, more particularly, to proximal struts within the proximal cell 420 and along a first proximal anchor segment 434 and a second proximal anchor segment 436. For example, the first end 474 can be attached to a first anchor eyelet 438 and the second end 476 can be attached to a second anchor eyelet 440. The first slot 486 is configured to correspond and receive a joint or interconnection between the first anchor segment 437 and the proximal cell 420 and the second slot 488 is configured to correspond and receive a joint between the second anchor segment 436 and the proximal cell 420. With this arrangement, the second member 454 can be attached to a proximal portion of the frame 402 with additional portions sewn to the frame 402, similar to the sewing shown in FIG. 11A.

Referring to FIGS. 12A, 12B, 13A and 13B, the first member 452 includes a longitudinal length dimension L1, a width dimension W1 and a depth dimension D1. Similarly, the second member 454 includes a longitudinal length dimension L2, a width dimension W2 and a depth dimension D2. The depth and width for each of the first and second member 452 and 454 may be, but is not limited to, a substantially similar dimension. As depicted, the length L1 of the first member 452 may be greater than the length L2 of the second member 454, however, note that the first member 452 is employed as two barriers or layers comprising the first portion 462 and second portion 464 each having a length of about L/2 (i.e., one half of L). Further, each respective length L1 and L2 is substantially greater than any other noted width or depth dimension of the tissue growth members. The depth D1 and D2 of the respective first member 452 and the second member 454 is substantially greater than the width W1 and W2 of each of the first member 452 and the second member 454. For example, the respective width W1 and W2 of the first and second member 452 and 454 may be approximately 1 mm to 3 mm and, preferably, between about 1 mm and 1.5 mm. The respective depth D1 and D2 of the first member 452 and the second member 454 may be approximately 3 mm to 10 mm and, preferably, between about 4 mm and 6 mm. As such, the depth dimension D1 and D2 may be substantially larger than the width dimension W1 and W2 and more particularly, may be in the order often times greater than each width dimension W1 and W2. Each of the respective depth dimensions D1 and D2 of the first and second member 452 and 454 is an important aspect of the invention, as will be set forth further below.

Further, as depicted in FIGS. 12A and 12B, according to an aspect of the present invention, the first member 452 and second member 454 positioned on the frame 402 extends substantially out-of-plane or substantially perpendicular relative to a plane 442 or flat configuration of the frame 402. The depths D1 and D2 of the first and second members 452 and 454 may each be three to twenty-five times greater than the depth-thickness DT of the frame 402 and, preferably eight to seventeen times greater than the depth-thickness DT of the frame 402. With this arrangement, when the closure device 400 is positioned within the PFO tunnel (not shown in FIG. 12A or 12B) with the first and second lateral sides of the closure device 400 expanding outward, the upper and lower walls of the PFO tunnel come into contact with the tissue growth member (since the tissue growth member 450 extends substantially perpendicular to the plane 442 of the frame 402) to, thereby, induce tissue growth thereto. In this manner, the first member 452 alone may provide the closure necessary in the PFO tunnel with the first portion 462 of the first member 452 providing a first layer of tissue growth and the second portion 464 of the first member 452 providing a second layer of tissue growth within the PFO tunnel. In addition, the second member 454 may provide an additional layer or third layer of tissue growth and closure to the PFO tunnel.

Further, due to the variability between different PFO tunnels, the first member 452 and the second member 454 together in their respective strategic locations attached to the frame 402 may provide greater success in closing any given PFO tunnel. For example, fenestrations or other surface variations may be present in any given PFO tunnel. The second member 454 is strategically positioned at a proximal portion of the frame 402 and, specifically, along portions of the proximal anchors to address potential issues involving fenestrations or other surface variations in a PFO tunnel.

The respective depth dimension D1 and D2 of the first member 452 and the second member 454, extending substantially perpendicular to the substantially planar or flat configuration of the frame 402, provides structure that advantageously maintains substantial contact with the tissue in the PFO tunnel to induce tissue growth through the first and second member 452 and 454 and to the tissue in the PFO tunnel. Further, due to the resilient, flexible and self expanding characteristics of the first and second member 452 and 454 extending out-of-plane, such first and second members may slightly fold or compress so as to maintain contact with the tissue in the PFO tunnel. The flexible nature of the first and second member 452 and 454, may maximize the surface area in contact with the tissue in the PFO tunnel despite the dynamic nature of the heart.

Figure 14:
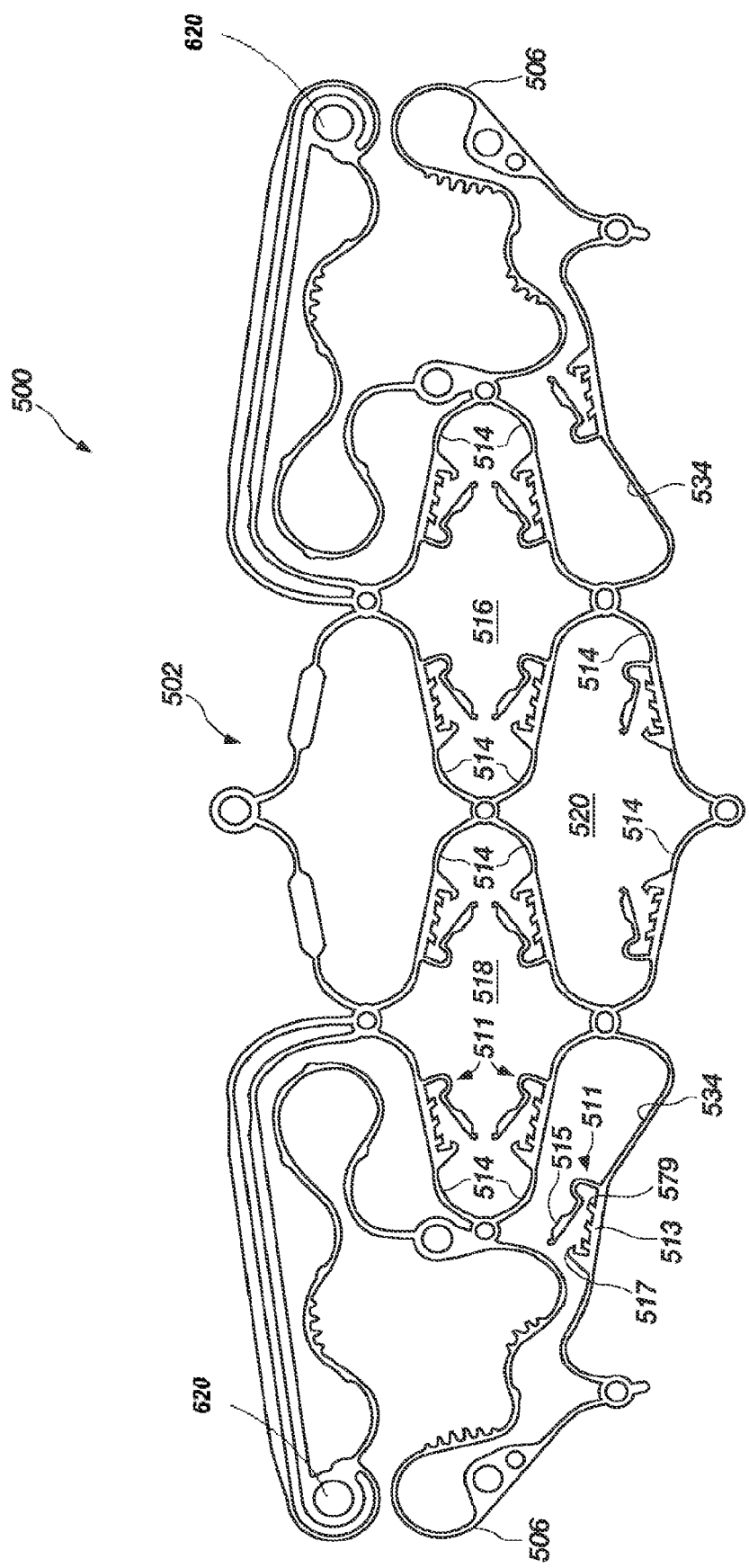
FIG. 14 illustrates another embodiment of a frame of a closure device having clips for attaching an ingrowth material thereto.

FIG. 14 illustrates another embodiment of a frame 502 of a closure device 500. In particular, in this embodiment, the frame 502 is substantially similar to the frame of the previous embodiment, except this frame 502 includes multiple clips 511 positioned at strategic locations on the frame 502. The clips 511 are configured to grasp and attach, for example, the first member 452 and the second member 454 (FIGS. 13A and 13B) to the frame 502. Each clip 511 includes a base 513 and a cantilevered lever arm 515 that can be displaced to engage an arm latch 517 extending from the base 513. The base 513 may also include nubs 519 to provide assisted traction in holding a tissue growth member (not shown in FIG. 14). It should be noted that a tissue growth member, such as, for example the first member 452 and second member 454 (depicted in FIGS. 13A and 13B), may be employed with the frame 502.

As depicted, each strut 514 of the first central cell 516 and the second central cell 518 can include a clip 511. Further, the proximal cell 520 can include a clip 511 on the inside wall portion of the two most proximal struts 514 of the proximal cell 520. In addition, each proximal anchor 506 can include a clip 511 along the inside wall portion of a proximal anchor segment 534. In this manner, similar to that depicted in the embodiment of FIG. 12A, the first member 452 and the second member 454 can be attached to the frame 502 of this embodiment by utilizing the clips 511. If desired, the first member 452 and the second member 454 may be additionally secured to the frame by sewing the ends and mid portion to corresponding eyelets, as set forth in the previously described embodiment. This embodiment of the frame 502 with clips 511 for attaching the first member 452 and second member 454 (FIG. 12A) may substantially stream-line manufacturing processes by eliminating, or at least substantially reducing, the sewing of the tissue growth member to the frame, thereby, saving time and increasing through-put in the manufacture of the closure device.

In one embodiment, the clips 511 may each be a seamless and unitary structure of the frame 502. Such a seamless structure can be employed by laser cutting the frame with each of the clips cut therewith from a flat sheet of metal, such as Nitinol metal. In this manner, the frame 502 of the closure device 500 can employ clips (that are seamless and unitary to the frame structure) to attach a tissue growth member, such as foam, as previously described.

Figure 15:
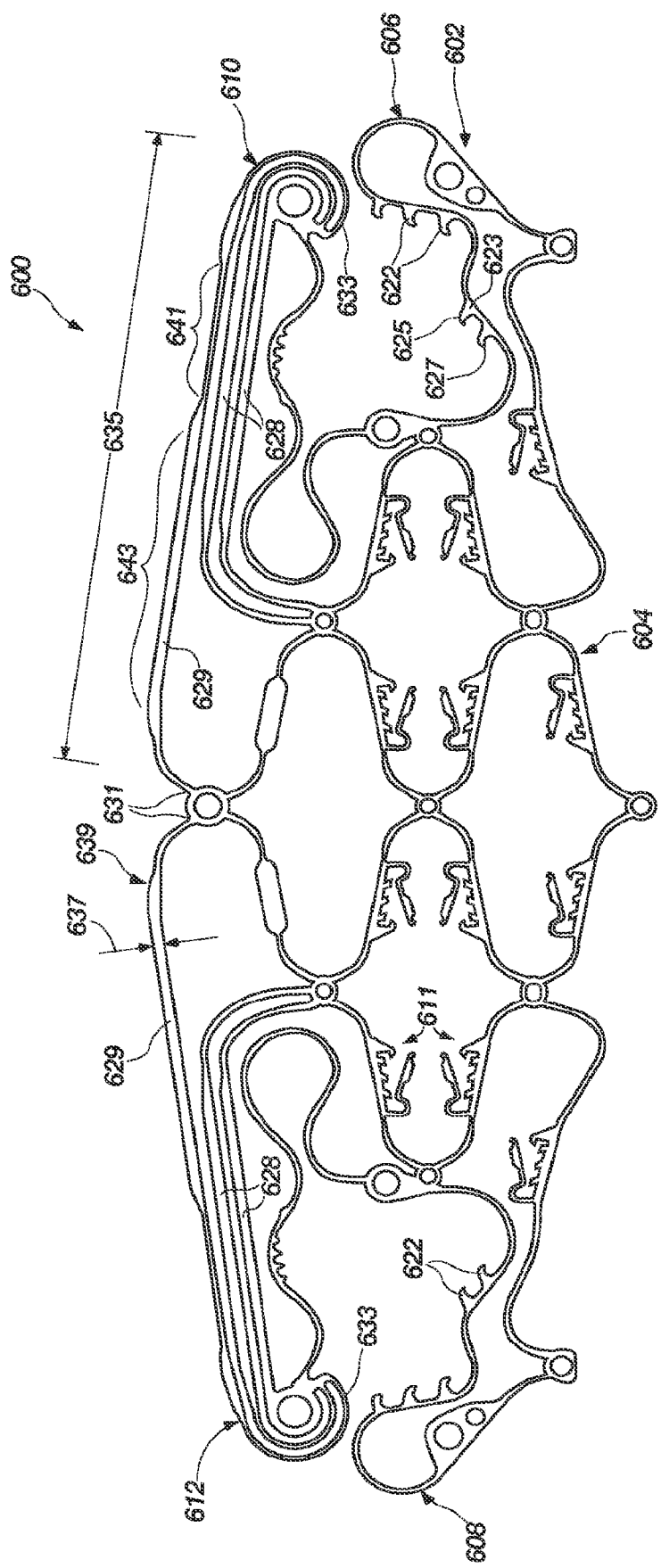
FIG. 15 illustrates another embodiment of a frame of a closure device with clips and an additional beam at a distal side of the closure device.

FIG. 15 illustrates another embodiment of a frame 602 of a closure device 600. This embodiment may be similar to the previous embodiments in many respects, except this frame 602 may include an additional beam or distal reinforcing segment 629 for each distal anchor to provide additional strength to the distal anchors as well as a different configuration for some of the engaging members 622 on each of the proximal anchors. This embodiment also includes clips 611 for clipping the tissue growth member (not shown) to the frame 602, which clips 611 may be oriented differently from the previously described embodiment on the proximal side of both the proximal anchors as well as the central portion. As in the previous embodiments, the frame 602 may include a central portion 604 with a first proximal anchor 606 and a second proximal anchor 608 extending from the proximal side of the central portion 604, and a first distal anchor 610 and a second distal anchor 612 extending from the distal side of the central portion 604.

As previously set forth, this embodiment includes an additional beam or an additional distal reinforcing segment 629 for each of the first distal anchor 610 and the second distal anchor 612. Each distal reinforcing segment 629 may extend from a distal node or distal end 631 of the central portion 604 of the frame 602 and connect adjacent the indicator 620 at the distal end 633 of the other more proximal segments 628 of the first distal anchor 610 and the second distal anchor 612. Further, each distal reinforcing segment 629 can extend laterally from the distal end 631 of the central portion 604 to extend at least partially along-side the more proximal reinforcing segments 628 in a substantially parallel manner.

Furthermore, each of the distal reinforcing segments 629 can include a longitudinal length dimension 635, a width dimension 637 and a depth dimension (not shown in FIG. 15). The length dimension 637, in the expanded configuration can be substantially linear with each end portion having a curvilinear or arcuate portion, the curvilinear portion curving and extending proximally to a connection point. The width dimension 637 can include, for example, tapered portions 639 such that the width dimension changes at one or more portions along the length thereof. For example, the distal reinforcing segment 629 can include a first portion 641 and a second portion 643, the first portion 641 having a smaller width dimension than the second portion 643, a tapered portion providing the transition between the first portion 641 and the second portion 643. Along the length of the distal reinforced segment 629 there can be several tapered portions or changes in width. The depth dimension of the distal reinforced segment 629 may be similar to the depth dimension of other portions of the frame (e.g., depth-thickness DT shown in FIG. 12B).

Further, each distal reinforcing segment 629 of the first distal anchor 610 and the second distal anchor 612 can be substantially coplanar with each other such that they are each in a substantially flat configuration. In another embodiment, each distal reinforcing segment 629 can be substantially coplanar with the central portion 604 and the other segments 628 of each distal anchor as well as substantially coplanar with the proximal anchors of the frame 602 such that the frame sits in a substantially flat configuration.

With the distal reinforcing segments 629 of this embodiment, the closure device 600 can more readily maintain a stable position within a tissue opening, such as in a PFO in the heart, to resist pull-through and disengagement from a deployed position. For example, pull-through can occur when a physician deploys the closure device 600 in a PFO and the physician manually pulls on the handle of the delivery device (not shown in FIG. 15) to determine if the closure device is firmly positioned within the PFO. Such reinforcing segments, cumulatively or in combination, provide resistance to pull-through so the physician can have a more affirmative indication that the closure device is stabilized with the PFO through increased resistance. Such resistance to pull-through may provide two to three times greater resistance than the previous embodiments of the closure device that do not include the additional distal reinforcing segment 629 of this embodiment. Furthermore, as previously set forth, certain portions of the distal reinforcing segments 629 may include a width dimension 637 greater than other portions along the length dimension 635 or may include tapered portions 639. Such characteristics in the distal reinforcing segments 629 provide for greater rigidity along certain portions of the length than on other portions, the portions with a greater width having the greater rigidity of the distal reinforced segments. In this manner, the closure device 600 can be deployed and refracted, in and out of the catheter or delivery device, over numerous iterations without causing undue fatigue, stress or hardening within the struts and segments of the frame 602. Such tapered portions 639 are calculated to distribute and manipulate the stress of the struts and segments of the frame 602 when being deployed and/or when placed in a constricted orientation in, for example, the tip portion of a catheter to maximize the strength of the struts and segments while minimizing the mass and size of the frame 602.

As previously set forth, the currently described embodiment may include engaging members 622, or otherwise referred to as miniature anchors, on the distal side of both the first proximal anchor 606 and the second proximal anchor 608. More particularly, according to one aspect of the present invention, the engaging members 622 exhibit a wave-crest configuration or profile. Such a wave-crest configuration includes a base portion 623, a peak portion 625 and a tip portion 627. The base portion 623 may extend from a strut or segment of the frame 602 and, in this embodiment, the distal surface of, for example, the first proximal anchor 606 or the second proximal anchor 608. The peak portion 625 extends from the base portion 623 and can be sized and configured to include a curved surface (without a sharp point) or rather, an atraumatic surface. Such curved peak portion 625 is specifically sized and configured to engage tissue without piercing the tissue that it engages. The tip portion 627 of the wave-crest profile extends downward or back away from the peak portion 625 and provides an edge 619 (see FIG. 16A) having a depth dimension (not shown) that extends substantially transverse to the plane of the closure device. The depth dimension of the edge 619 may be substantially the same as the depth dimension of the anchor segment from which the engaging member extends. In the presently considered embodiment, the depth dimension is substantially larger than the width dimension of the proximal anchor segments (as previously discussed in relation to aspect ratio), thereby, providing a substantial edge, along the depth dimension, sized and configured to aggressively engage tissue, but not configured to pierce tissue.

Figure 16A:
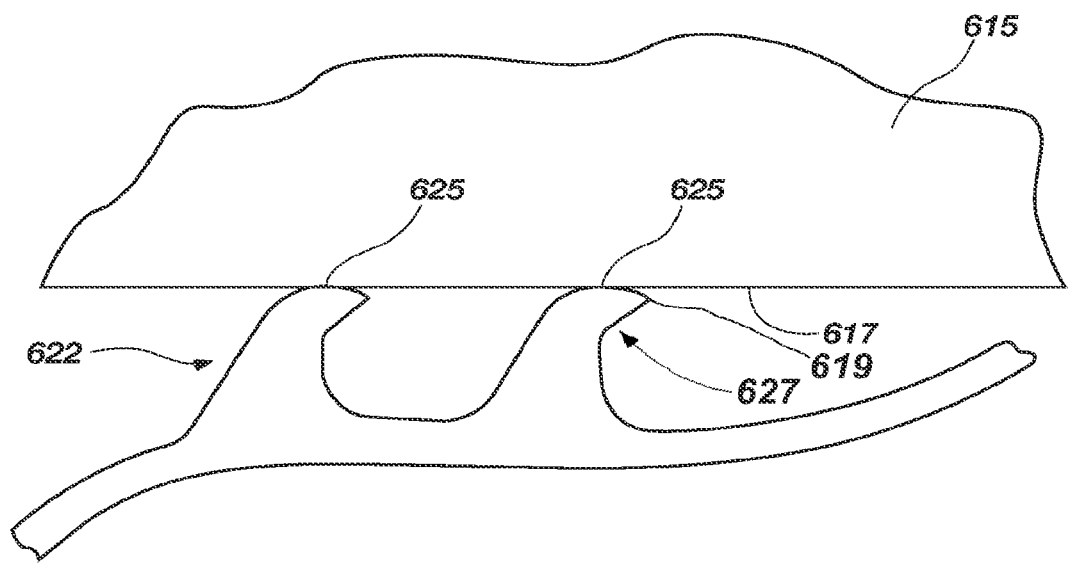
FIGS. 16A and 16B illustrate engaging members of the closure device, depicting the engaging members adjacent a catheter and tissue, respectively, according to an embodiment of the present invention.
Figure 16B:
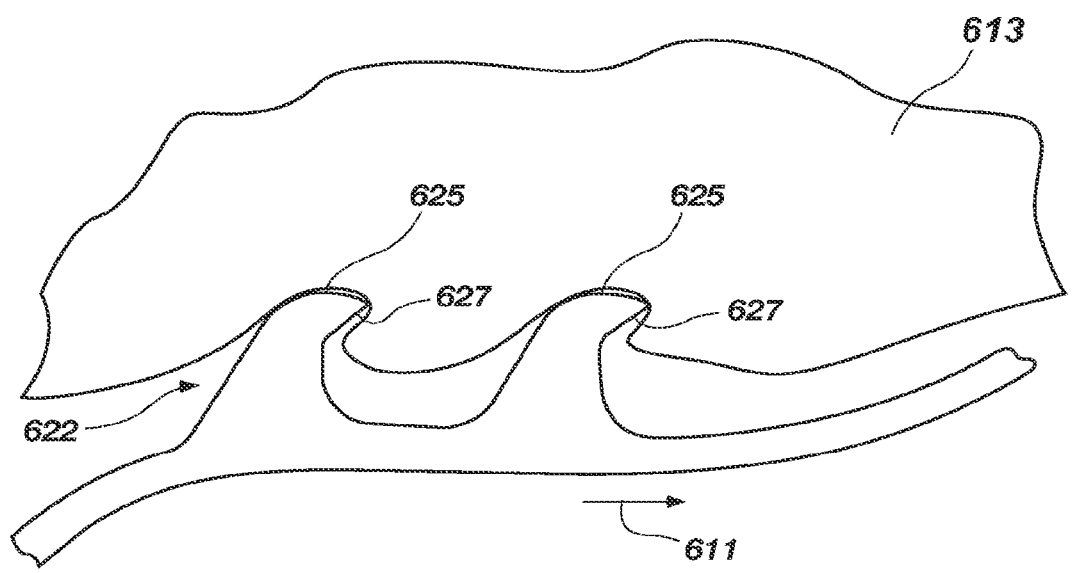

With reference now to FIG. 16A, the engaging members 622, with the wave-crest configuration, are shown when the closure device is pulled into a catheter 615. In the constricted, undeployed configuration within the catheter 615, the engaging members 622 are positioned directly against the inside surface 617 of the catheter 615. With the wave-crest configuration, the peak portion 625 is positioned against the semi-hard surface of the catheter 615. If the peak portion included an acute oblique point, the closure device may not readily be able to be moved to a deployed orientation due to such point catching or causing resistance against the surface of the catheter as the closure device is displaced relative to the inside surface 617 of the catheter 615. However, the curved, blunt surface of the peak portion 625 provides minimal resistance during such displacement to facilitate ready deployment of the closure device from the catheter 615. On the other hand, as depicted in FIG. 16B, when the engaging members 615 with the wave crest configuration are in contact and positioned against tissue 613, the tissue is conformable with such wave crest configuration, such that the curved surface of the peak portion 625 provides an atraumatic surface specifically designed to engage, but not pierce the tissue 613 such as shown.

Further, the wave crest configuration will provide aggressive engagement or resistance in the direction of arrow 611 at the tip portion 627 and edge of the engaging members 622. With this arrangement, the engaging members 622 having the wave crest configuration provide advantages when in contact with a hard surface, such as the inner surface 617 of a catheter 615 so as to limit resistance while providing aggressive engagement with tissue 613 in a predetermined direction, arrow 611; atraumatic engagement at the peak portion 625 of the wave-crest configuration; and, further, non-piercing/atraumatic engagement at the tip portion 627 of the wave crest configuration when deployed adjacent tissue 613 or within a tissue structure, such as a PFO.

Figure 17:
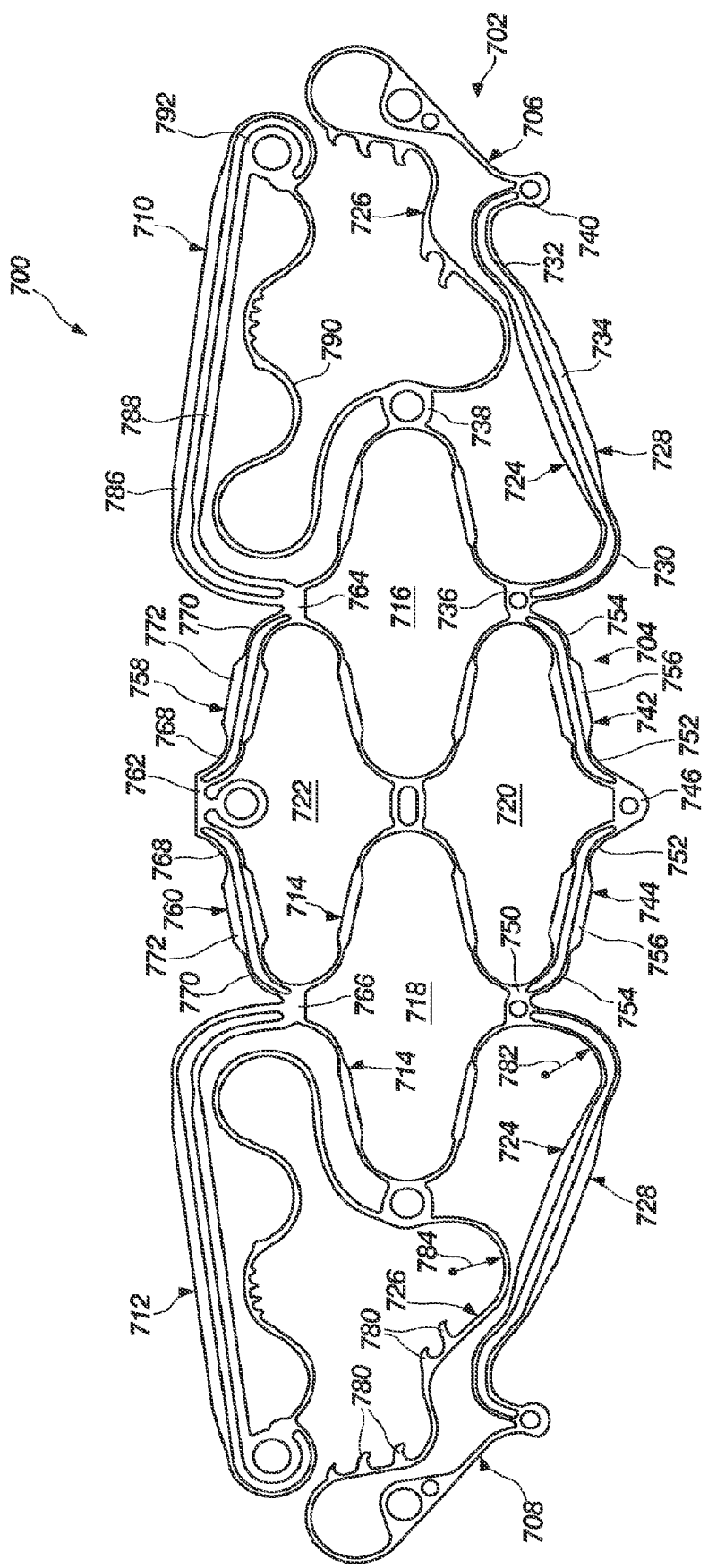
FIG. 17 illustrates another embodiment of a frame of a closure device, according to the present invention.

With reference now to FIG. 17, another embodiment of a frame 702 of a closure device 700 is shown. The frame 702 of this embodiment is similar in many respects to a frame depicted in previous embodiments (e.g., FIG. 3A). For example, the frame 702 may include a central portion 704 with first and second proximal anchors 706 and 708 extending from a proximal portion of the central portion 704. The frame also includes first and second distal anchors 710 and 712 extending from a distal portion of the central portion 704. The central portion 704 may include a plurality of segments or struts 714 that define a multi-cellular structure. In one embodiment, the multiple struts 714 may define four cells: a first central cell 716, a second central cell 718, a proximal cell 720 and a distal cell 722, the multiple struts 714 collectively defining the central portion 704 of the frame 702. Similar to previous embodiments, the frame 702 may be in the form of a generally flat plane or substantially planar (or may be described as including or exhibiting a substantially flat configuration) such that the frame may remain in a substantially flat configuration when constricted within the tip portion of the catheter (not shown) or at any other deployment stage. In one embodiment, the first and second proximal anchors 706 and 708 may be co-planar with the central portion 404. In another embodiment, the first and second distal anchors 710 and 712 may be co-planar with the central portion 704.

In one embodiment, each cell may include four struts 714 defining a particular cell. Adjacent cells may share one or more struts 714. For example, cells having four struts may include at least two struts 714 that are common with two adjacent cells. Further, each cell may include one or more nodes configured to interconnect adjacent struts 714. Furthermore, cells having four struts 714 may include four nodes associated therewith, each node being associated with two adjacent struts. Such nodes may additionally interconnect struts 714 of adjacent cells or, in other words, one cell may share one or more nodes of adjacent cells. In one embodiment, the central portion 704 can include nine nodes: eight peripheral nodes and one central node. The interconnection of the nodes the struts 714 may define, in whole or in part, the multi-cellular structure of the central portion 704, the central node interconnecting the struts 714 for each of the four cells. With this arrangement, the multi-cellular structure, including nodes and struts, is configured to maximize outward expansion force while also minimizing the material or mass required for such expansion force.

Further, as in the previous embodiments, the first and second proximal anchors 706 and 708 may include multiple proximal anchor segments to define at least a portion of a closed periphery. Likewise, the first and second distal anchors 710 and 712 may include multiple distal anchor segments to define at least a portion of a closed periphery. For example, the first proximal anchor 706 may include a first proximal anchor segment 724 extending from a right lateral node 736 of the proximal cell 720 and a second proximal anchor segment 726 extending from a right-lateral node 738 of the first central cell 716, the first and second proximal anchor segments 724 and 726 extending to and interconnecting at a proximal anchor node 740. Such proximal anchor node 740 may also be employed as an attachment portion for tethering the frame to the delivery system (not shown). Thus, a closed periphery or a closed loop is defined by the anchor segments 724 and 726 in conjunction with nodes 736, 738 and 740.

In one embodiment, the first and second proximal anchors 706, 708 may include an additional proximal anchor segment or a third proximal anchor segment 728. Such third proximal anchor segment 728 may extend, similar to the first proximal anchor segment 724, between the right lateral node 736 of the proximal cell 720 to the proximal anchor node 740. Further, the third proximal anchor segment 728 may extend substantially parallel to or along with the first proximal anchor segment 724. In one embodiment, the third proximal anchor segment 728 may include a first flexible portion 730 and a second flexible portion 732 with a rigid portion 734 extending therebetween. Each flexible portion may include a taper along a portion of a length of such flexible portion such that the tapering may extend or transition to the rigid portion 734. The first proximal anchor segment 724, extending along-side the third proximal anchor segment 728, may include similar structural features as that of the third proximal anchor segment 728 or generally mirror the structural features thereof. In this manner, the third proximal anchor segment 728 for each of the first and second proximal anchors 706 and 708 provides additional resistance to the proximal anchors to prevent the closure device from moving or migrating to the left atrium of the heart (not shown in FIG. 17) when deployed in a PFO.

In addition, the frame 702 of the closure device 700 may include one or more struts or dual struts extending alongside or substantially parallel with each other on the proximal side of the proximal cell 720. In comparison to the frame shown in FIG. 3A, the frame depicted in FIG. 17 exhibits a first additional strut 742 extending between a proximal node 746 of the proximal cell 720 to a right lateral node 736 of the proximal cell 720. Similarly, a second additional strut 744 can extend between the proximal node 746 of the proximal cell 720 to a left lateral node 750 of the proximal cell 720. Further, similar to the other struts of the central portion 704, the first and second additional struts 742 and 744 may include a first flexible portion 752 and a second flexible portion 754 with an intermediate rigid portion 756 therebetween. The flexible portions 752 and 754 may taper or otherwise transition to the rigid portion 756. With this arrangement, the first and second additional struts 742 and 744, in combination to the adjacent interior proximal struts of the proximal cell 720, are configured to provide additional resistance in comparison to a single strut configuration (e.g., see FIG. 3A) within the central portion 704 to minimize any potential of the closure device moving or migrating to the left atrium.

Furthermore, in another embodiment, the frame 702 may include dual distal struts of the distal cell 722 of the central portion 704 that may extend along-side or substantially parallel with each other. More specifically, the distal cell 722 may include a first additional strut 758 and a second additional strut 760, each extending from a distal node 762 of the distal cell 722 to a right lateral node 764 of the distal cell 722 and a left lateral node 766 of the distal cell 722, respectively. Such first and second additional struts 758 and 760 of the distal cell 722 can each include a first flexible portion 768 and a second flexible portion 770 with a rigid portion 772 therebetween. The flexible portions may be sized and configured to taper to or otherwise transition to the rigid portion 772. In this manner, the dual struts of the distal cell 722 are sized and configured to provide additional resistance, in comparison to a single strut configuration of the central portion 704, in further preventing the closure device 700 from moving to the right atrium, or provide additional pull through resistance when tethered to the delivery system.

In addition, the embodiment depicted in FIG. 17 may provide engaging members 780 having a wave-crest configuration such as described above with respect to FIGS. 15, 16A and 16B. The engaging members 780 may be positioned along the second proximal anchor segment 726 (along a distal surface of such segment) for both the first and second proximal anchors 706, 708. As in the previous embodiment, the engaging members 780 are sized and configured to not pierce the tissue, but rather, aggressively engage the tissue if the closure device 700 moves toward the left atrium, thereby, substantially preventing potential migration or movement of the closure device 700 into the left atrium. In one embodiment, as shown, engagement members having a wave-crest configuration may be located on the proximal anchors 706 and 708, but not on the distal anchors 710 and 712. In another embodiment, engagement members having a wave-crest configuration may be located on any one, or on all of the anchors.

In another embodiment, in comparison to the embodiment depicted in FIG. 3A, the first and second proximal anchors 706, 708 exhibit an increased length. With such increased length, the first proximal anchor segment 724 and the second proximal anchor segment 726, at their initial curvilinear extension from the central portion 704, include a first radius 782 and a second radius 784, respectively, that is greater than the corresponding radii of the previous embodiment. Such larger radii provides a reduction in the strain exhibited in the first and second proximal anchor segments 724 and 726 when the frame 702 is moved between an expanded configuration and a strained or stressed configuration, such as when constricted within a catheter. It should be noted that the first radius 782 and the second radius 784 of the first and second proximal anchor segments 724, 726, respectively, may be substantially similar. Additionally, the first and second radii 782 and 784 may be as large as, or larger than the radius of the strut or segment ends of adjacent cells (e.g., 716, 718 and 720).

In accordance with another aspect of the present invention, in one embodiment, the structural lengths, tapers, rigid portions, etc. between various portions, i.e., struts, anchor segments, etc., of the frame 702 may be similar with other like or similar portions in order to effectively and substantially symmetrically facilitate movement between a strained position within a catheter and an expanded position deployed from a catheter. For example, in one embodiment, the structural components for one half of the frame or right side of the frame may be equivalent or substantially a mirror image of the structural components for the other half or left side of the frame. In another embodiment, the struts 714 that define each of the four cells of the central portion 704, may be substantially similar in length, with substantially equivalent flexible portions, tapered portions and rigid portions. In another embodiment, the distal most struts 714 in the distal cell 722 include a substantially similar length. In another embodiment, the distal struts 714 of the first and second central cell 716 and 718 (which include the proximal struts of the distal cell 722) include a substantially similar length. Similarly, in another embodiment, the proximal struts 714 of the first and second central cell 716 and 718 include a substantially similar length. In still another embodiment, the proximal most struts 714 of the proximal cell 720 include a substantially similar length.

Furthermore, the various anchor segments of the first and second proximal anchors 706 and 708 and the first and second distal anchors 710 and 712 include common relationships in order to effectively and substantially symmetrically strain or stress the frame 702 when is constrained within an associated catheter or other delivery device. For example, the first proximal anchor segment 724 is substantially the same length as the second proximal anchor segment 726. The first proximal anchor segment 724 extending between the right lateral node 736 of the proximal cell 720 and the proximal anchor node 740. The second proximal anchor segment 726 extending between the right lateral node 738 of the first central cell 716 and the proximal anchor node 740. It should be noted that the undulations in the second proximal anchor segment 726 (that also include the engaging members 780) facilitate the range of motion of the first and second proximal anchors 706 and 708 in being strained and moved in a proximal direction when being constricted within a catheter (similar to that depicted in FIG. 3B). When constricted within a catheter, the undulations typically may not completely straighten and, therefore, the second proximal anchor segment 726 may be slightly longer than the first proximal anchor segment 724. In this manner, the symmetrical characteristics between the various structural components of the frame minimize fatigue in the frame and maximize a smooth transition between an un-deployed and deployed state of the frame 702 with respect to the catheter.

Further, in another embodiment, first and second distal anchors 710 and 712 of the frame 702 may exhibit common lengths within their respective distal anchor segments. For example, first and second distal anchor segments 786 and 788 or reinforcing segments, in combination with the length of the strut 714 between the right lateral node 738 of the first central cell 716 and the right lateral node 764 of the distal cell 722, may be substantially similar in length to a third distal anchor segment 790 extending between the right lateral node 738 of the first central cell 716 and a distal anchor node 792. As shown, the third distal anchor segment 790 exhibits undulations to increase the length of the third distal anchor segment 790 and allow the distal anchors with the necessary range of motion to move to the constricted position in a catheter or other delivery device. When in the constricted position, the undulations of the third distal anchor segment 790 may not completely straighten and, thus, the third distal anchor segment 790 may be slightly longer than the length of the first and second distal anchor segments 786 and 788 plus the length of the strut 714, as previously set forth.

Figure 18:
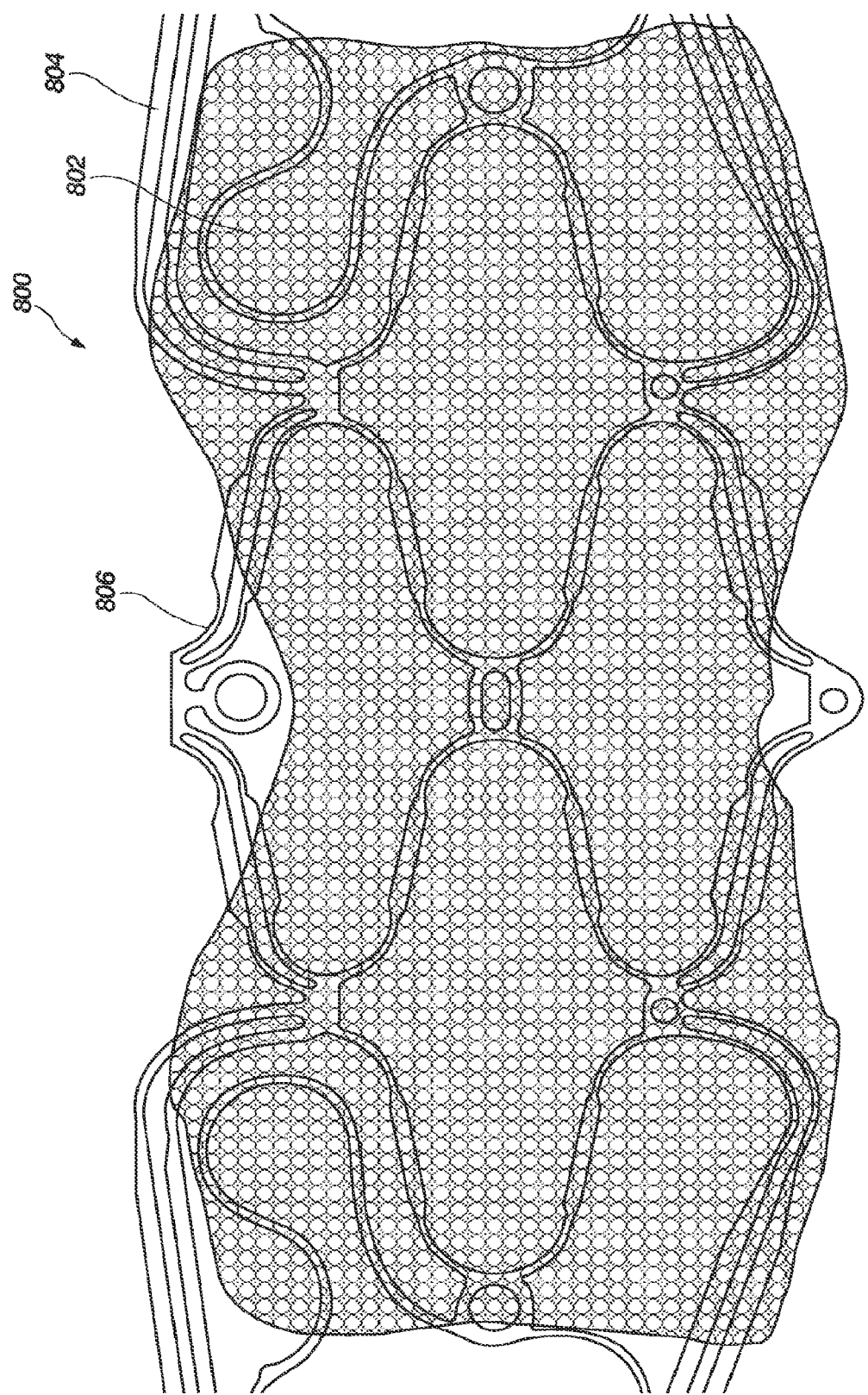
FIG. 18 illustrates another embodiment of a tissue growth member attached to a closure device, according to the present invention.
Figure 19:
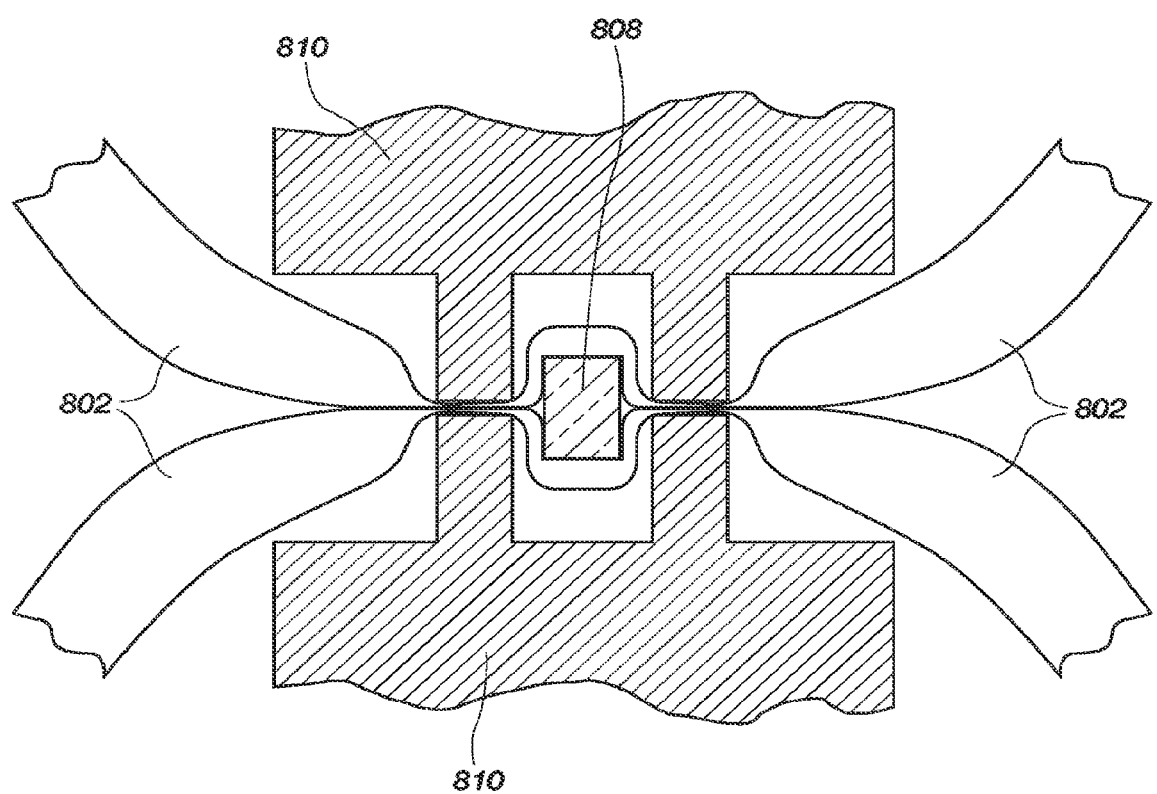
FIG. 19 illustrates an embodiment for attaching the tissue growth member to the closure device.

Now referring to FIGS. 18 and 19, another embodiment of a closure device 800, depicting an unfinished process for attaching a tissue growth member 802 to a frame 804 of the closure device 800. In particular, in this embodiment, the tissue growth member 802, may be thermally welded to, or about, the central portion 806 of the frame 804. As depicted, the tissue growth member 802, such as foam, may be thermally welded to one or more struts 808 of the central portion 806. The process of thermally welding may include a welding fixture 810 sized and configured to clamp down, for example, on both sides of a strut 808 within the central portion 806 and with two layers of a tissue growth member 802 therebetween. The welding fixture 810 heats and fuses the tissue growth member 802 together at an approximate predetermined temperature to, thereby, attach the tissue growth member 802 to particular struts of the central portion 806 of the frame 804. Once the tissue growth member 802 is thermally welded to the frame, as depicted in FIG. 18, the tissue growth member 802 may then be cut or otherwise trimmed to a desired configuration, generally similar to that depicted in FIG. 12A or any other suitable configuration. It should be noted that the configuration may vary slightly from that depicted in FIG. 12A due to the tissue growth member being thermally welded to both sides of selected struts 808 or the central frame segments. Further, various slits or openings may be cut or formed within the thermally welded foam (for example, within the cells of the central portion 806) that will facilitate the tissue growth member to readily conform between a constrained orientation within a catheter, and an expanded, un-constrained (or minimally constrained, as-deployed) orientation.

Figure 20:
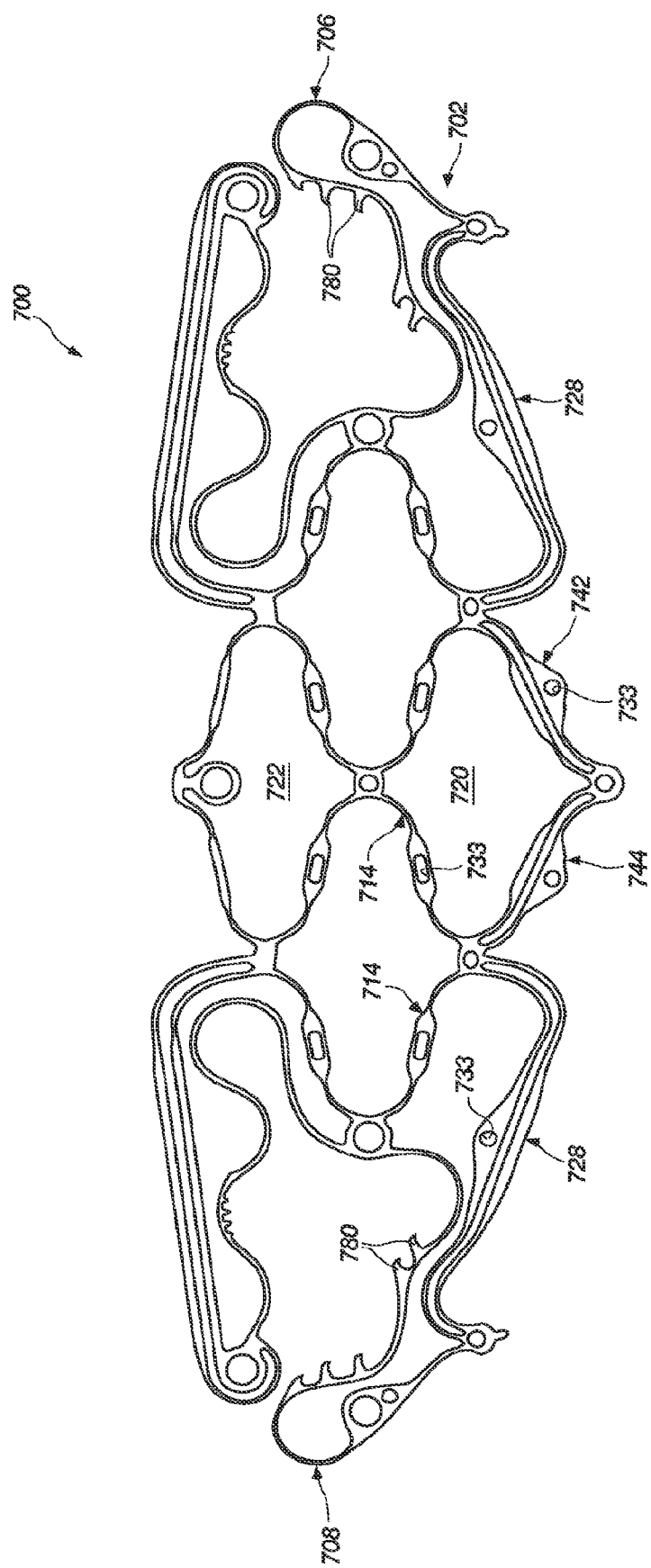
FIG. 20 illustrates another embodiment of a frame of a closure device, according to the present invention.

With respect to FIG. 20, another embodiment of the previously described closure device 700 is provided. This embodiment is similar to that depicted and described with respect to FIG. 17, except this embodiment does not include the first and second additional struts 758 and 760 (FIG. 17) distal the distal cell 722 of the frame 702. This embodiment does, however, include the first and second additional struts 742 and 744 or central frame segments proximal the proximal cell 720. Further, this embodiment also may exhibit the additional proximal anchor segments or the third proximal anchor segment 728 for each of the first proximal anchor 706 and the second proximal anchor 708. Further, the frame may also include the engaging members 780, as previously described, on the first and second proximal anchors. In addition, this embodiment may define various eyelets 733 in the first and second proximal anchors 706, 708. The eyelets 733 may also be defined in the central frame segments or central frame struts 714 as well as the first and second additional struts 742, 744. Such eyelets 733 may be employed, for example, for sewing a tissue growth member (not shown) thereto. The frame 702 of the closure device 700, depicted in this embodiment, may include a tissue growth member for inducing tissue in-growth, as previously described, that may be attached, for example, via stitching, sewing, clipping, or by adhesive with a similar configuration as that depicted and described with respect to FIGS. 12A and 12B, or it may be thermally attached as previously set forth in conjunction with FIGS. 19 and 20.

As previously set forth, the frame may be a generally flat frame or substantially planar or includes a substantially flat configuration when in an expanded configuration and resists movement out of such substantially planar or flat configuration. Further, the first and second proximal anchors may be co-planar with the central portion. Likewise, the first and second distal anchors may be co-planar with the central portion. Further, the frame may remain in a substantially flat configuration when constricted within the tip portion of the catheter or at any other deployment stage.

The present invention may be embodied in other specific forms without departing from its spirit or essential characteristics. The described embodiments are to be considered in all respects only as illustrative and not restrictive. Various features of one embodiment may be described in features of other embodiments. The scope of the invention is, therefore, indicated by the appended claims rather than by the foregoing description. All changes which come within the meaning and range of equivalency of the claims are to be embraced within their scope. Thus, it should be understood that the invention is not intended to be limited to the particular forms disclosed. Rather, the invention includes all modifications, equivalents, and alternatives falling within the spirit and scope of the invention as defined by the following appended claims.

What is claimed is:

1. An expandable medical device deployable at least partially within a hole defined in a tissue structure between a first atrium and a second atrium of a heart, the hole defining an axis oriented axially through the hole, the expandable medical device comprising:
a frame configured to maintain a substantially flat configuration as said frame transitions and self-expands from a non-deployed state to an intended, as deployed state, said frame configured to be oriented parallel to, or extending along, the axis of the hole when in the intended, as-deployed state within the tissue structure, said frame comprising a central portion, at least one proximal anchor and at least one distal anchor, said central portion comprising a plurality of frame segments defining a multi-cellular structure, said at least one proximal anchor and said at least one distal anchor each configured to extend substantially coplanar with said central portion in the intended, as-deployed state with said at least one proximal anchor configured to extend in the first atrium and said at least one distal anchor configured to extend in the second atrium;
wherein said plurality of frame segments define four cells of the multi-cellular structure, each frame segment extending directly to and defining a length between nodes such that each cell is defined by four frame segments and only four nodes, each node connecting adjacently extending frame segments, and wherein said plurality of frame segments each include arcuate portions extending along the length of each frame segment such that a collective length of the arcuate portions extends along a majority of the length of each frame segment, and each cell of said multi-cellular structure is defined by said plurality of frame segments such that each cell includes a common frame segment of an adjacent cell.

2. The medical device as recited in claim 1, wherein said frame is configured to assume said substantially flat configuration lying in a first plane, said frame being configured to resist movement out of said first plane of the substantially flat configuration.

3. The medical device as recited in claim 1, wherein said at least one proximal anchor comprises engaging members configured to engage tissue.

4. The medical device as recited in claim 1, further comprising a tissue growth member configured to be attached to said frame and configured to induce tissue growth.

5. The medical device as recited in claim 4, wherein the tissue growth member comprises an elongated configuration positioned along the central portion of the frame and configured to be positioned in the hole and oriented transverse to the axis of the hole.

6. The medical device as recited in claim 4, wherein the tissue growth member comprises:
a first elongate tissue growth portion positioned along the central portion of the frame and configured to be positioned in the hole and oriented transverse to the axis of the hole; and
a second elongate tissue growth portion positioned proximal to the first elongate tissue growth portion, the second elongate tissue growth portion configured to be oriented transverse to the axis of the hole.

7. The medical device as recited in claim 4, wherein the tissue growth member comprises a polymeric material.

8. A medical device deployable at least partially within a hole defined in a tissue structure, the hole defining an axis oriented axially through the hole, the medical device comprising:
a framework configured to maintain a substantially flat configuration as said framework transitions and self-expands from being constricted within a catheter to being deployed from the catheter, said framework configured to be oriented parallel to, or extending along, the axis of the hole when in a state for intended deployment within the tissue structure, said framework comprising a central portion and at least one anchor extending from said central portion, said central portion including central frame segments having a length and a width, wherein the width of at least one of said central frame segments varies along at least a portion of the length of said at least one of said central frame segments in a tapered configuration;
wherein said central frame segments extend to define a multi-cellular structure having four cells, the length of each central frame segment extending directly to and between nodes such that each cell is defined by four central frame segments and only four nodes, each node connecting adjacently extending central frame segments, and wherein said central frame segments each include arcuate portions extending along the length of each central frame segment such that a collective length of the arcuate portions extends along a majority of the length of each central frame segment, and each cell includes a common central frame segment of an adjacent cell.

9. The medical device as recited in claim 8, wherein said at least one anchor comprises a first proximal anchor and a second proximal anchor each including a plurality of anchor frame segments, wherein at least two of the anchor frame segments extend substantially parallel to each other along at least a portion of their respective lengths for each of the first proximal anchor and the second proximal anchor.

10. The medical device as recited in claim 8, wherein said at least one anchor comprises engaging members configured to engage tissue.

11. The medical device as recited in claim 8, further comprising a tissue growth member configured to be attached to said framework and configured to induce tissue growth.

12. The medical device as recited in claim 11, wherein the tissue growth member comprises an elongated configuration positioned along the central portion of the framework and configured to be positioned in the hole and oriented transverse to the axis of the hole.

13. The medical device as recited in claim 11, wherein the tissue growth member comprises a polymeric material.

14. A medical device deployable at least partially within a hole defined in a tissue structure, the hole defining an axis oriented axially through the hole, the medical device comprising:

a framework configured to maintain a substantially flat configuration as said framework transitions and self-expands from being constricted within a catheter to being deployed from the catheter, said framework configured to be oriented parallel to, or extending along, the axis of the hole when in a state for intended deployment within the tissue structure, said framework comprising a central portion and at least one anchor extending from said central portion, said central portion including central frame segments defining a multi-cellular structure, at least one of said central frame segments including a longitudinal length dimension and having an aspect ratio of a depth dimension to a lateral width dimension of at least 2 to 1, wherein said depth dimension is defined to extend perpendicular relative to said substantially flat configuration of said framework;

wherein said central frame segments define four cells of said multi-cellular structure, a length of each central frame segment extending directly to and between nodes such that each cell is defined by four central frame segments and only four nodes, each node connecting adjacently extending central frame segments, and wherein said central frame segments each include arcuate portions extending along the length of each central frame segment such that a collective length of the arcuate portions extends along a majority of the length of each central frame segment, and each cell of said multi-cellular structure is defined by said central frame segments such that each cell includes a common central frame segment of an adjacent cell.

15. The medical device as recited in claim 14, wherein said at least one anchor comprises a first proximal anchor and a second proximal anchor each including a plurality of anchor frame segments, wherein at least two of the anchor frame segments extend substantially parallel to each other along at least a portion of their respective lengths for each of the first proximal anchor and the second proximal anchor.

16. The medical device as recited in claim 14, wherein said at least one anchor comprises engaging members configured to engage tissue.

17. The medical device as recited in claim 14, further comprising a tissue growth member configured to be associated with said framework and configured to induce tissue growth.

18. The medical device as recited in claim 17, wherein the tissue growth member comprises an elongated configuration positioned along the central portion of the framework and configured to be positioned in the hole and oriented transverse to the axis of the hole.

19. The medical device as recited in claim 17, wherein the tissue growth member comprises a polymeric material.

* * * * *